United States Patent
Curran et al.

(10) Patent No.: US 6,455,699 B1
(45) Date of Patent: *Sep. 24, 2002

(54) CAMPTOTHECIN ANALOGS AND METHODS OF PREPARATION THEREOF

(75) Inventors: Dennis P. Curran, Pittsburgh, PA (US); Hubert Josien, Jersey City, NJ (US); Bom David, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/633,561

(22) Filed: Aug. 7, 2000

Related U.S. Application Data

(63) Continuation of application No. 08/921,102, filed on Aug. 29, 1997, now Pat. No. 6,150,343, which is a continuation-in-part of application No. 08/436,799, filed on May 8, 1995, now abandoned, which is a continuation-in-part of application No. 08/085,190, filed on Jun. 30, 1993, now abandoned.

(51) Int. Cl.[7] .............................. C07F 7/08; A61P 35/00; A61K 31/695
(52) U.S. Cl. ........................................................ 546/14
(58) Field of Search ............................................. 546/14

(56) References Cited

U.S. PATENT DOCUMENTS

| | | |
|---|---|---|
| 5,468,859 A | 6/1993 | Fortunak |
| 5,700,939 A | 6/1993 | Fortunak |

(List continued on next page.)

FOREIGN PATENT DOCUMENTS

| | | |
|---|---|---|
| WO | WO98/07727 | 2/1998 |
| WO | WO98/35940 | 8/1998 |

OTHER PUBLICATIONS

Curran, D.P. and Liu, H., "New 4+1 Radical Annula- (List continued on next page.)

*Primary Examiner*—Mark L. Berch
(74) *Attorney, Agent, or Firm*—Bartony & Hare

(57) ABSTRACT

The present invention provides generally a compound having the following general formula (1):

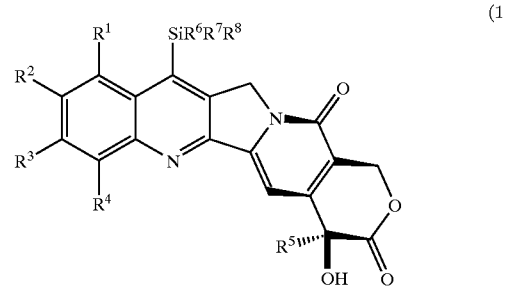

wherein $R^1$ and $R^2$ are independently the same or different and are hydrogen, an alkyl group, an alkenyl group, a benzyl group, an alkynyl group, an alkoxyl group, an aryloxy group, an acyloxy group, —OC(O)OR$^d$, wherein R$^d$ is an alkyl group, a carbamoyloxy group, a halogen, a hydroxyl group, a nitro group, a cyano group, an azido group, a formyl group, a hydrazino group, an acyl group, an amino group, —SR$^c$, wherein, R$^c$ is hydrogen, an acyl group, an alkyl group, or an aryl group, or $R^1$ and $R^2$ together form a group of the formula —O(CH$_2$)$_n$O— wherein n represents the integer 1 or 2; $R^3$ is H, F, a halogen atom, a nitro group, an amino group, a hydroxyl group, or a cyano group; or $R^2$ and $R^3$ together form a group of the formula —O(CH$_2$)$_n$O— wherein n represents the integer 1 or 2; $R^4$ is H, F, a C$_{1-3}$ alkyl group, a C$_{2-3}$ alkenyl group, a C$_{2-3}$ alkynyl group, or a C$_{1-3}$ alkoxyl group; $R^5$ is a C$_{1-10}$ alkyl group, or a propargyl group; and $R^6$, $R^7$ and $R^8$ are independently a C$_{1-10}$ alkyl group, a C$_{2-10}$ alkenyl group, a C$_{2-10}$ alkynyl group, an aryl group or a —(CH$_2$)$_N$R$^9$ group, wherein N is an integer within the range of 1 through 10 and $R^9$ is a hydroxyl group, alkoxy group, an amino group, an alkylamino group, a dialkylamino group, a halogen atom, a cyano group or a nitro group; and pharmaceutically acceptable salts thereof.

8 Claims, 6 Drawing Sheets

U.S. PATENT DOCUMENTS

| | | | |
|---|---|---|---|
| 6,211,371 | B1 | 5/1995 | Curran |
| 5,744,605 | A | 6/1996 | Curran |
| 6,252,079 | B1 | 7/1997 | Curran |
| 5,910,491 | A * | 6/1999 | Hausheer ............... 546/14 |
| 6,057,303 | A * | 5/2000 | Haridas ............... 546/14 |
| 6,150,343 | A * | 11/2000 | Curran ............... 546/14 |

OTHER PUBLICATIONS tions—A Formal Total Synthesis of (+/−)−Campothecin," J. Am. Chem Soc., 114, 5863–5864 (1992), Published Jul. 1, 1992.

Curran, D.P., "The Camptothecins—A reborn Family of Antitumor Agents", J. Chin. Chem. Soc., 40, 1–6 (1993). Published Feb. 1993.

Curran, D.P. et al., "Recent Applications of Radical Reactions in Natural Product Synthesis," Pure Appl. Chem., 65, 1153–1159 (1993). Published Jun. 1993.

Curran, D.P. et al., "Cascade Radical Reactions of Isonitriles: A Second–Generation Synthesis of (20S)–Camptothecin, Topotecan, Irinotecan, and GI–147211C," Angew. Chem. Int. Ed, 34, 2683–2684 (1995). Published Jan. 5, 1996.

Curran, D.P., Liu, H.; Josien, H; Ko, S.B., "Tandem Radical Reactions of Isonitriles with 2–pyrdonyl and other aryl radicals: Scope and Limitations, and a First Generation Sunthesis of (+/−)–Camptothecin," Tetrahedron, 52, 11385–11404 (1996). Published Aug.1996.

Josien, H. and Curran, D.P., "Synthesis of (S)–mappicine and Mappicine Ketone Via Radical Cascade Reaction of Isonitiriles," Tetrahedron, 53, 8881–8886 (1997), Published Jun. 30, 1997.

Liu, H. et al., "Selective N–Functionalization of 6–Substituted–2–Pyridones," Tetrahedron Letters, 36:49, 8917–8920 (1995).

* cited by examiner

Synthesis of 3

CAMPTOTHECIN ANALOGS AND METHODS OF PREPARATION THEREOF

RELATED APPLICATIONS

This application is a continuation of U.S. patent application Ser. No. 08/921,102, filed Aug. 29, 1997 U.S. Pat. No. 6,150,343 which is a continuation-in-part application of U.S. patent application Ser. No. 08/436,799, filed May 8, 1995 abandoned which is a continuation-in-part application of U.S. patent application Ser. No. 08/085,190, filed Jun. 30, 1993 abandoned the disclosures of which are incorporated herein by reference.

GOVERNMENT INTERESTS

This invention was made with government support under grant #5 RO1 GM33372 awarded by the National Institutes of Health. The government has certain rights in this invention.

FIELD OF THE INVENTION

The present invention relates to novel compounds and methods of preparation thereof and, particularly, to silyl camptothecin derivatives or analogs and to methods of preparation of such silyl camptothecin analogs.

BACKGROUND OF THE INVENTION (20S)-Camptothecin (CPT, see below) and its derivatives are some of the most promising agents for the treatment of solid tumors by chemotherapy. See, for example, Wall, M. E. et al, *J. Ethnopharmacol.*, 51, 239 (1996); *Camptothecin: New Anticancer Agents;* Potmesil, M. and Pinedo, H., Eds.; CRC, Boca Raton, Fla. (1995); Bonneterre, J., *Bull. Canc.*, 82, 623 (1995); Sinha, D. K., *Drugs*, 49, 11 (1995). This natural alkaloid was first isolated in 1966 from the extract. of a Chinese plant, *Camptotheca accuminata,* by Wall. Wall, M. E. et al, *J. Am. Chem. Soc.*, 88, 3888 (1966). As depicted below, camptothecin has a fused ring system generally comprising a pyrrolo[3,4-b]quinoline system (rings ABC) fused to a 2-pyridone ring (ring D), which, in turn, is fused to a lactone ring (ring E).

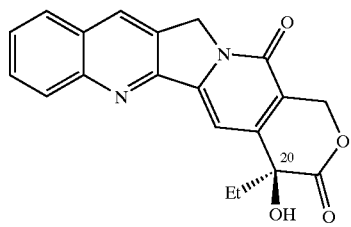

(20S)-camptothecin, CPT
Rings are labeled A–E from left to right

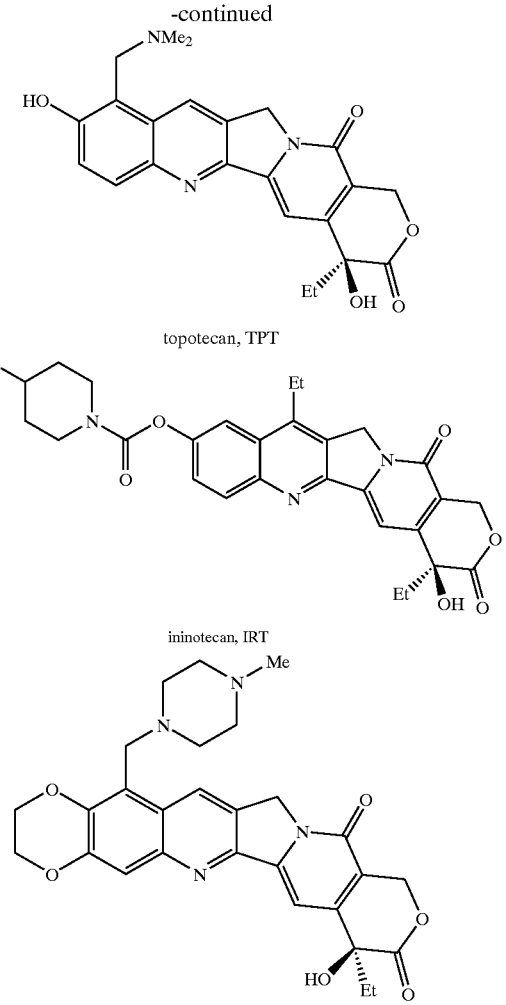

topotecan, TPT irinotecan, IRT

GI-147211C

Camptothecin belongs to the family of topoisomerase I poisons. See, for example, Froelich-Ammon, S. J. et al., *J. Biol. Chem.*, 270, 21429 (1995). Research to date strongly suggests that this molecule acts by interfering with the unwinding of supercoiled DNA by the cellular enzyme topoisomerase I, an enzyme which is usually overexpressed in malignant cells. In the highly replicating cancer cells, this triggers a cascade of events leading to apoptosis and programmed death. See Slichenmyer, W. J. et al., *J. Natl. Cancer Inst.*, 85, 271 (1993). Recent advances at the molecular pharmacology level are reviewed in Pommier, Y. et al., *Proc. Natl. Acad. Sci. USA*, 92, 8861 (1995).

Camptothecin's initial clinical trials were limited by its poor solubility in physiologically compatible media. Moreover, early attempts to form a water-soluble sodium salt of camptothecin by opening the lactone ring with sodium hydroxide resulted in a compound having a poor antitumor activity. It was later reported that the closed lactone-form is an absolute requisite for antitumor activity. See Wani, M. C. et al., *J. Med. Chem.*, 23, 554 (1980). More recently, structure-activity studies have identified analogous compounds with better solubility and better antitumor activity. For example, topotecan (TPT) and irinotecan (IRT) have recently been approved for sale in the United States, while GI-147211C is in late stage clinical trials. These analogs are effective against a variety of refractory solid tumors such as malignant melanoma, stomach, breast, ovarian, lung and colorectal cancers, and seem particularly promising for the treatment of slow-dividing cancer lines. See, for example, Kingsbury, W. D. et al., *J. Med. Chem.*, 34, 98 (1991); Sawada, S. et al., *Chem. Pharm. Bull.*, 39, 1446 (1991); Luzzio, M. J. et al., *J. Ned. Chem.*, 38, 395 (1995); Abigerges, D. et al., *J. Clin. Oncol.*, 13, 210 (1995). Furthermore, synergistic or additive effects have been observed in combination therapies with cisplatin, irradiation, or hyperthermia. See Fukuda, M. et al., *Canc. Res.*, 56, 789 (1996); Goldwasser, F. et al., *Clin. Canc. Res.*, 2, 687 (1996); Wang, D. S. et al., *Biol. Pharm. Bull.*, 19, 354 (1996).

Although most research has focused on the development of water-soluble derivatives of camptothecin, new formulations, such as lipid-complexation, liposomal encapsulation, and wet milling technology have recently been developed. Such formulations result in new therapeutic opportunities for poorly water-soluble camptothecins. See Daoud, S. S. et al., *Anti-Cancer Drugs*, 6, 83 (1995); Merisko-Liversidge, E. et al., *Pharm. Res.*, 13, 272 (1996); and Pantazis, P., *Leukemia Res.*, 19, 775 (1995). An attractive feature of these formulations is their impact on drug biodistribution. Sugarman and coworkers have recently reported that while free camptothecin achieves the greatest concentration in the pulmonary parenchyma, lipid-complexed camptothecin has the highest concentration in the gastrointestinal tract. These results open new and interesting perspectives for the treatment of colon cancer. See Sugarman, S. M. et al., *Canc. Chemother. Pharmacol.*, 37, 531 (1996). Another interesting aspect of using insoluble camptothecin analogs is that they are usually more active than their water-soluble congeners and seem less likely to create drug-induced resistance, probably because they are not substrates of the p-glycoprotein multi-drug transporter. See Pantazis, P., *Clin. Canc. Res.*, 1, 1235 (1995).

In this context, new camptothecin analogs that combine good to excellent anti-tumor activities with different solubility and biodistribution profiles could play a crucial role in the therapeutic arsenal for the treatment of various types of cancers.

Given the proven beneficial biological activity of camptothecin and analogs thereof, it is desirable to develop additional camptothecin analogs and methods of preparation of camptothecin analogs.

SUMMARY OF THE INVENTION

The present invention provides generally a compound having the following formula (1):

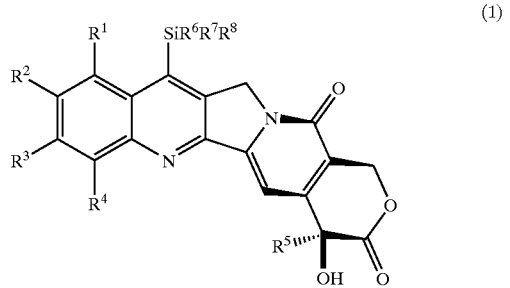

$R^1$ and $R^2$ are independently the same or different and are preferably hydrogen, an alkyl group, an alkenyl group, an alkynyl group, an alkoxyl group, an aryloxy group, an acyloxy group, —OC(O)OR$^d$, wherein R$^d$ is an alkyl group, a carbamoyloxy group, a halogen, a hydroxyl group, a nitro group, a cyano group, an azido group, a formyl group, a hydrazino group, an acyl group, an amino group, —SR$^c$, wherein, R$^c$ is hydrogen, an acyl group, an alkyl group, or an aryl group, or $R^1$ and $R^2$ together form a group of the formula —O(CH$_2$)$_n$O— wherein n represents the integer 1 or 2.

$R^3$ is preferably H, a halogen, a nitro group, an amino group, a hydroxyl group, or a cyano group. $R^2$ and $R^3$ can also together form a group of the formula —O(CH$_2$)$_n$O— wherein n represents the integer 1 or 2.

$R^4$ is preferably H, F, a $C_{1-3}$ alkyl group, a $C_{2-3}$ alkenyl group, a $C_{2-3}$ alkynyl group, or a $C_{1-3}$ alkoxyl group. $R^5$ is preferably a $C_{1-10}$ alkyl group. A preferred alkyl group is an ethyl group. Preferred substituted alkyl groups for $R^5$ include an allyl group, a propargyl and a benzyl group.

$R^6$, $R^7$ and $R^8$ preferably are independently (the same or different) a $C_{1-10}$ alkyl group, a $C_{2-10}$ alkenyl group, a $C_{2-10}$ alkynyl group, or an aryl group. A preferred substituted alkyl group for $R^6$, $R^7$ and $R^8$ is a —(CH$_2$)$_N$R$^9$ group, wherein N is an integer within the range of 1 through 10 and $R^9$ is a hydroxyl group, an alkoxyl group, an amino group, a halogen atom, a cyano group or a nitro group. Preferred amino groups for $R^9$ include alkylamino groups and a dialkylamino groups.

The terms "alkyl", "aryl" and other groups refer generally to both unsubstituted and substituted groups unless specified to the contrary. Unless otherwise specified, alkyl groups are preferably $C_1$–$C_{15}$ (that is, having 1 to 15 carbon atoms) alkyl groups, and more preferably $C_1$–$C_{10}$ alkyl groups, and can be branched or unbranched, acyclic or cyclic. The above definition of an alkyl group and other definitions apply also when the group is a substituent on another group (for example, an alkyl group as a substituent of an alkylamino group or a dialkylamino group). The term "aryl" refers to phenyl or napthyl. As used herein, the terms "halogen" or "halo" refer to fluoro, chloro, bromo and iodo.

The term "alkoxyl" refers to —OR$^d$, wherein R$^d$ is an alkyl group. The term "aryloxy" refers to —OR$^e$, wherein R$^e$ is an aryl group. The term acyl refers to —OCR$^f$. The term "alkenyl" refers to an unsaturated radical with preferably 2–15 carbon atoms, more preferably with 3–10 carbon atoms (—C≡CHR$^g$). The term "alkynyl" refers to an unsaturated radical preferably with 2–15 carbon atoms, more preferably with 3–10 carbon atoms (—C≡CR$^h$).

The groups set forth above, can be substituted with a wide variety of substituents to synthesize camptothecin analogs retaining activity. For example, alkyl groups may preferably be substituted with a group or groups including, but not limited to, a benzyl group, a phenyl group, an alkoxyl group, a hydroxyl group, an amino group (including, for example, free amino groups, alkylamino, dialkylamino groups and arylamino groups), an alkenyl group, an alkynyl group and an acyloxy group. In the case of amino groups (—NR$^a$R$^b$), $R^a$ and $R^b$ are preferably independently hydrogen, an acyl group, an alkyl group, or an aryl group. Acyl groups may preferably be substituted with (that is R$^f$ is) an alkyl group, a haloalkyl group (for example, a perfluoroalkyl group), an alkoxyl group, an amino group and a hydroxyl group. Alkynyl groups and alkenyl groups may preferably be substituted with (that is, R$^g$ and R$^h$ are preferably) a group or groups including, but not limited to, an alkyl group, an alkoxyalkyl group, an amino alkyl group and a benzyl group.

The term "acyloxy" as used herein refers to the group

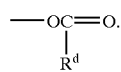

The term "carbamoyloxy" as used herein refers to the group

Amino and hydroxyl groups may include protective groups as known in the art. Preferred protective groups for amino groups include tert-butyloxycarbonyl, formyl, acetyl, benzyl, p-methoxybenzyloxycarbonyl, trityl. Other suitable protecting groups as known to those skilled in the art are disclosed in Greene, T., Wuts, P. G. M., *Protective Groups in Organic Synthesis,* Wiley (1991), the disclosure of which is incorporated herein by reference.

In general, $R^1$, $R^2$, $R^3$, $R^6$, $R^7$ and $R^8$ are preferably not excessively bulky to maintain activity of the resultant camptothecin analog. Preferably, therefore, $R^1$, $R^2$, $R^3$, $R^6$, $R^7$ and $R^8$ independently have a molecular weight less than approximately 250. More preferably $R^1$, $R^2$, $R^3$, $R^6_1$, $R^7$ and $R^8$ independently have a molecular weight less than approximately 200.

Some of the camptothecin analogs of the present invention can be prepared for pharmaceutical use as salts with inorganic acids such as, but not limited to, hydrochloride, hydrobromide, sulfate, phosphate, and nitrate. The camptothecin analogs can also be prepared as salts with organic acids such as, but not limited to, acetate, tartrate, fumarate, succinate, citrate, methanesulfonate, p-toluenesulfonate, and stearate. Other acids can be used as intermediates in the preparation of the compounds of the present invention and their pharmaceutically acceptable salts.

For purification purposes, the E-ring (the lactone ring) may be opened with alkali metal such as, but not limited to, sodium hydroxide or calcium hydroxide, to form opened E-ring analogs of compounds of formula (1). The intermediates thus obtained are more soluble in water and may be purified to produce, after treatment with an acid, a purified form of the camptothecin analogs of the present invention.

The E-ring may also be modified to produce analogs of compounds of formula (1) with different solubility profiles in water or other solvents. Methods to achieve this goal include, but are not limited to, opening the E-ring with an water-soluble amino group or functionalyzing the hydroxyl group at position 20 of the E-ring with a water-soluble group such as a polyethylene glycol group. The analogs thus prepared act as pro-drugs. In other words, these analogs regenerate the compounds of formula (1) (with the closed E-ring structure) when administered to a living organism. See, Greenwald, R. B. et al., *J. Med. Chem.,* 39, 1938 (1996).

The present invention also provides a method of treating a patient, which comprises administering a pharmaceutically effective amount of a compound of formula (1) or a pharmaceutically acceptable salt thereof. The compound may, for example, be administered to a patient afflicted with cancer and/or leukemia by any conventional route of administration, including, but not limited to, intravenously, intramuscularly, orally, subcutaneously, intratumorally, intradermally, and parenterally. The pharmaceutically effective amount or dosage is preferably between 0.01 to 60 mg of the compound of formula (1) per kg of body weight. More preferably, the pharmaceutically effective amount or dosage is preferably between 0.1 to 40 mg of the compound of formula (1) per kg of body weight. In general, a pharmaceutically effective amount or dosage contains an amount of a compound of formula (1) effective to diaplay antileukemic and/or antitumor (anticancer) behavior. Pharmaceutical compositions containing as an active ingredient a compound of formula (1) or a pharmaceutically acceptable salt thereof in association with a pharmaceutically acceptable carrier or diluent are also within the scope of the present invention.

The present invention also provides a pharmaceutical composition comprising any of the compounds of formula (1) and a pharmaceutically acceptable carrier. The composition may contain between 0.1 mg and 500 mg of the compound of formula (1), and may be constituted into any form suitable for the mode of administration.

DETAILED DESCRIPTION OF THE INVENTION

Compounds

Among the compounds of formula (1), those having the (S)-configuration at position 20 of the E-ring are preferred for pharmaceutical use.

$R^1$ and $R^2$ are preferably and independently (the same or different) H, a hydroxyl group, a halo group, an amino group, a nitro group, a cyano group, a $C_{1-3}$ alkyl group, a $C_{1-3}$ perhaloalkyl group, a $C_{1-3}$ alkenyl group, a $C_{1-3}$ alkynyl group, a $C_{1-3}$ alkoxyl group, a $C_{1-3}$ aminoalkyl group, a $C_{1-3}$ alkylamino group, a $C_{1-3}$ dialkylamino group, or $R^1$ and $R^2$ together form a group of the formula —O(CH$_2$)$_n$O— wherein n represents the integer 1 or 2. More preferably, $R^1$ and $R^2$ are independently (the same or different) H, a methyl group, an amino group, a nitro group, a cyano group, a hydroxyl group, a hydroxymethyl group, a methylamino group, a dimethylamino group, an ethylamino group, a diethylamino group, an aminomethyl group, a methylaminomethyl group, a dimethylaminomethyl group, and the like.

$R^3$ is preferably F, an amino group, or a hydroxyl group. $R^4$ is preferably H or F. $R^5$ is preferably an ethyl group. $R^6$, $R^7$ and $R^8$ are preferably independently (the same or different) a $C_{1-6}$ alkyl group, a phenyl group or a —(CH$_2$)$_N$R$^{10}$ group, wherein N is an integer within the range of 1 through 6 and $R^{10}$ is a halogen or a cyano group.

Method of Preparation

Figure 1:
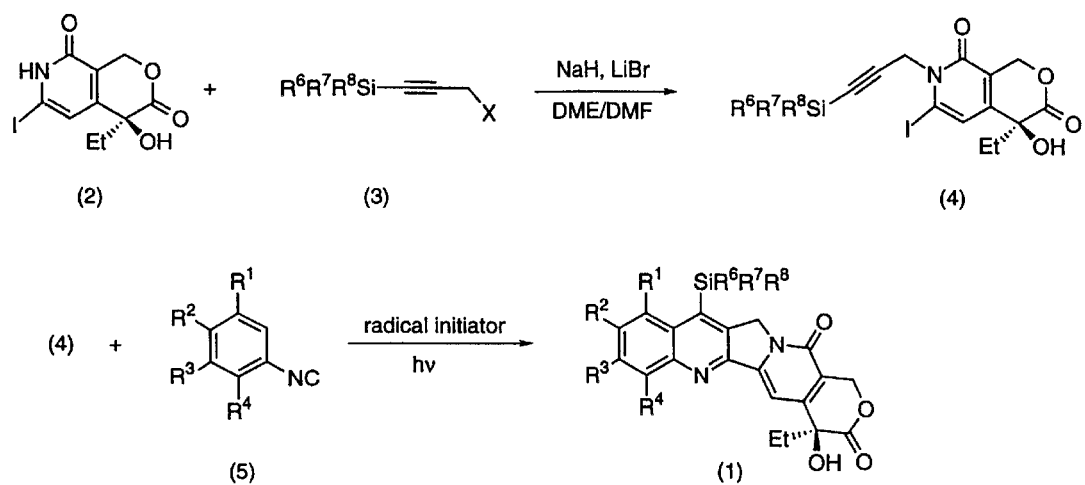
FIG. 1 is an illustration of a general synthetic scheme for the preparation of compounds of formula 1.
Figure 1:
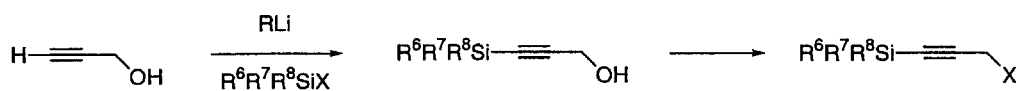

The compounds of the present invention can be prepared according to the general synthetic scheme shown in FIG. 1. In the synthetic scheme of FIG. 1, an iodopyridone 2 is first N-alkylated with a propargyl derivative 3 to produce radical precursor 4. Radical precursor 4 then undergoes a radical cascade with arylisonitrile 5 to generate product 1. The N-alkylation proceeds smoothly following optimized conditions. See Curran, D. P. et al., *Tetrahedron Lett.*, 36, 8917 (1995), the disclosure of which is incorporated herein by reference. The synthesis of iodopyridone 2 and the conditions of the radical cascade have been previously reported. The propargylating agent 3 is readily prepared by the standard silylation of the dianion of propargyl alcohol with a suitable sylating agent $R^6R^7R^8SiX$ followed by conversion of the propargyl alcohol to a leaving group such as a bromide, iodide or sulfonate. See Curran, D. P. et al., *Angew. Chem. Int. Ed. Engl.*, 34, 2683 (1995), the disclosure of which is incorporated herein by reference, and U.S. patent application Ser. No. 08/436,799, filed May 8, 1995, the disclosures of which are incorporated herein by reference.

Generally, various reagents can be used in the radical cascade including, but not limited to, hexamethyltin, hexamethyldisilane, or tetrakis(trimethylsilyl)silane. The source of energy for this reaction can be a sun lamp or an ultraviolet lamp. The temperature is preferably set between approximately 25 and 150° C. More preferably, the temperature is set at approximately 70° C. There are generally no limitations upon the choice of solvent used other than inertness to the radical cascade. Preferred solvents include benzene, toluene, acetonitrile, THF and tert-butanol. Also, there is very broad latitude in the choice of substituents on the alkyne and the isonitrile because of the mildness of the reaction conditions.

Figure 2:
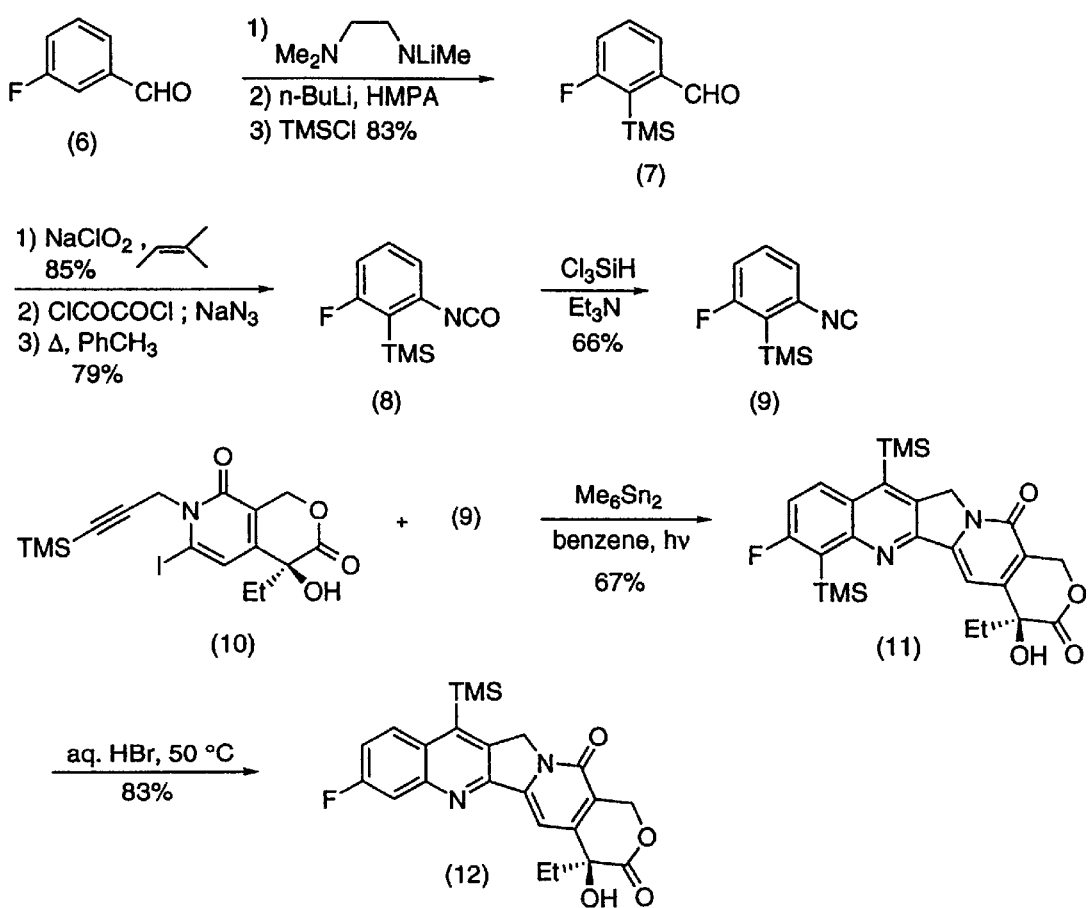
FIG. 2 is an illustration of a synthesis of (20S)-11-fluoro-7-trimethylsilylcamptothecin.

FIG. 2 illustrates an embodiment of a general synthetic scheme for the synthesis of (20S)-11-fluoro-7-trimethylsilylcamptothecin 12. A problem in this synthetic scheme is to control the regioselectivity of the radical cascade when both ortho positions in the arylisonitrile are available for cyclization (that is, $R^4$ is H in the final compound of formula 1). One solution to this problem relies upon the introduction of a trimethylsilyl group on the aryl isonitrile, (e.g. 3-fluoro-2-trimethylsilylphenyl isonitrile 9). The trimethylsilyl substituent blocks one of the ortho sites of the isonitrile toward cyclization and can be removed after the cascade reaction by hydrodesilylation.

In this example, the selectivity proceeds further in the sense that only one of the trimethylsilyl groups is removed in the last step.

Other embodiments of the general synthetic scheme for the preparation of several novel camptothecin derivatives are illustrated in FIGS. 3 to 6, and in the Examples.

The present invention provides a short and efficient synthetic scheme well suited to known structure-activity relationships in the camptothecin family. Indeed, the biological activity of the camptothecin skeleton is generally intolerant or has very little tolerance to substituents other than at the 7 and/or 9–11 positions. Following synthesis, these substituents are introduced via the alkynylderivative 3 and arylisonitrile 5, respectively.

Antitumor Activities

The antitumor activities of several compounds of formula 1 are shown in Table 1 and compared to those of several well known camptothecin analogs. The syntheses of the various exemplary compounds of the present invention set forth in Table 1 are discussed in further detail in an Example section following this section.

TABLE 1

Biological Activities of (20S)-7-Silyl-Camptothecin Derivatives.

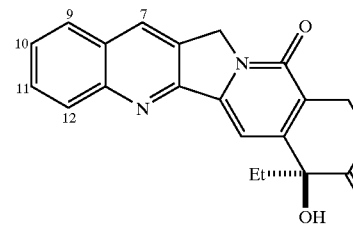

| Example | 7[a] | 9 | 10 | 11 | 12 | HL-60 | 833K | DC-3F | Enhancement of Topo I Mediated DNA Cleavage | Inhibition of Topo I mediated DNA relaxation |
|---|---|---|---|---|---|---|---|---|---|---|
| | | | | | | \multicolumn{3}{c}{Inhibition of cancer cell growth $IC_{50}$ (nM)} | | |
| CPT | H | H | H | H | H | 5 | 10 | 6–9 | +++ | +++ |
| IRT | Et | H | OPP[a] | H | H | 270 | 487 | 372 | – | – |
| 1 | TMS | H | H | H | H | 3.8 | 5.6 | 4.2 | ++++ | +++ |
| 2 | TBDMS | H | H | H | H | 0.12 | 1.2 | 2.9 | ++++ | +++ |
| 3 | TBDPS | H | H | H | H | 339 | 243 | 663 | ++ | + |
| 4 | TMS | H | OAc | H | H | 2.7 | | 6.7 | ++++ | +++++ |
| 5 | TMS | H | OH | H | H | 2.6 | 7.0 | 6.9 | ++++ | +++++ |
| 5a | Example 5 with opened E ring | | | | | 9.7 | 15.0 | 14.2 | +++ | + |
| 6 | TMS | H | OPP[a] | H | H | 66 | 214 | 256 | – | – |
| 7 | TMS | H | H | F | H | 0.75 | 0.92 | 2.0 | ++++ | +++++ |
| 7a | TMS | F | H | H | H | 3.0 | 2.9 | 8.2 | ++++ | ++++ |
| | TMS | H | H | F | H (2:1) | | | | | |
| 8 | TMS | H | NH$_2$ | H | H | 0.52 | 5.7 | 0.72 | – | – |
| 9 | TMS | H | H | NH$_2$ | H | 2.6 | 7.4 | 6.4 | – | – |
| 10 | TMS | H | NH$_2$ | F | H | 0.07 | 0.14 | 0.29 | ++++ | ++++ |
| 11 | TMS | H | H | F | F | 1.01 | 2.1 | 2.5 | +++ | +++ |
| | TMS | F | F | H | H (3/1) | | | | | |
| 12 | TIPS | H | H | H | H | 1506 | 10730 | 1038 | – | – |
| 13 | TES | H | H | H | H | 31.9 | 122 | 57.1 | – | – |
| 14 | DMNPS | H | H | H | H | 66.9 | 197 | 64.1 | – | – |

TABLE 1-continued

Biological Activities of (20S)-7-Silyl-Camptothecin Derivatives.

| Example | 7[a] | 9 | 10 | 11 | 12 | Inhibition of cancer cell growth $IC_{50}$ (nM) HL-60 | 833K | DC-3F | Enhancement of Topo I Mediated DNA Cleavage | Inhibition of Topo I mediated DNA relaxation |
|---|---|---|---|---|---|---|---|---|---|---|
| 15 | DMCPS | H | H | H | H | 0.91 | 2.7 | 2.7 | – | – |
| 16 | DMHPS | H | H | H | H | 2.1 | 5.4 | 2.3 | – | – |
| 17 | TBDMS | H | OAc | H | H | 1.86 | — | 3.57 | – | – |
| 18 | TBDMS | H | OH | H | H | 2.60 | — | 5.20 | – | – |

[a]OPP = irinotecan's pyrrolidinyl pyrrolidine carbamate;
TMS = trimethylsilyl;
TBDMS = t-butyldimethylsilyl;
TBDPS = t-butyldiphenyl silyl;
TES = triethylsilyl;
TIPS = triisopropylsilyl;
DMNPS = dimethylynorpinylsilyl;
DMCPS = dimethyl-3-cyanopropylsilyl;
DMHPS = dimethyl-3-halopropylsilyl;
[b]More active than CPT in S-180 in $BD_2F_1$ mice testing.
[c]More active than CPT in Lewis lung Carcinoma in $BD_2F1$ mice.

As illustrated in Table 1, the compounds of the present invention exhibit good to excellent antitumor activity as compared to camptothecin (CPT) and irinotecan (IRT).

Cytotoxicity Assays

The camptothecin derivatives were evaluated for their cytotoxic effects on the growth of HL-60 (human promyelocytic leukemic), 833K (human teratocarcinoma) and DC-3F (hamster lung) cells in vitro. The cells were cultured in an initial density of $5 \times 10^{-4}$ cell/ml. They were maintained in a 5% $CO_2$ humidified atmosphere at 37° C. in RPMI-1640 media (GIBCQ-BRL Grand Island, N.Y.) containing penicillin 100u/ml)/streptomycin (100 µg/ml) (GIBCO-BRL) and 10% heat inactivated fetal bovine serum. The assay was performed in duplicate in 96-well microplates. The cytotoxicity of the compounds toward HL-60 cells following 72 hr incubation was determined by XTT-microculture tetrazolium assay. Scudiero, D. A., et al., Cancer Res., 48, 4827 (1988), the disclosure of which is incorporated herein by reference. 2',3'-bis(-methoxy-4-nitro-5-sulfheny)-5-[(phenylamino)carbonyl]-2H-tetrazolium hydroxide (XTT) was prepared at 1 mg/ml in prewarmed (37° C.) medium without serum. Phenazine methosulfate (PMS) and fresh XTT were mixed together to obtain 0.075 mM PMS-XTT solution (25 µl of the stock 5 mM PMS was added per 5 ml of 1 mg/ml XTT). Fifty µl of this mixture was added to each well of the cell culture at the end of 72 hr incubation. After incubation at 37° C. for 4 hr., absorbance at 450 nm and 630 nm was measured with a microplate reader (EL340, Bio-Tek Instruments, Inc., Winooski, Vt.).

The cytotoxicity of the camptothecin compounds toward 833K teratocarcinoma solid tumor cells and DC-3F hamster lung cells was determined in 96-well microplates by a method described by Skehan et al. for measuring cellular protein content. Skehan et al., "New Colorometric Cytotoxicity Assay for Anticancer Drug Screening," J. Nat'l Cancer Inst., 82, 1107 (1990), the disclosure of which is incorporated herein by reference. Cultures were fixed with trichloroacetic acid and then stained for 30 minutes with 0.4% sulforhodamine B dissolved in 1% acetic acid. Unbound dye was removed by acetic acid washes, and the protein-bound dye was extracted with an unbuffered Tris base [tris (hydroxy-methyl)aminomethan] for determination of absorbance at 570 nm in a 96-well microplate reader. The experiments were carried out in duplicate using five to six concentrations of the drugs tested. Data were analyzed via computer software. See, Chou, J, and Chou, T. C., Dose-Effect Analysis With Microcomputers: Quantitation of $ED_{50}$, $LD_{50}$, Synergism, Antagonism, Low-Dose Risk, Receptor-Ligand Binding and Enzyme Kinetics, $2^{nd}$ ed., Biosoft, Cambridge (1987); and Chou, T. C., "The Median-Effect Principle and the Combination Index for Quantitation of Synergism and Antagonism," Synergism and Antagonism in Chemotherapy, Academic Press, San Diego, 61–102 (1991), the disclosures of which are incorporated herein by reference.

Topo I Mediated DNA Cleavage Assay

For DNA cleavage assay the reaction mixture comprised Tris-HCl buffer 10 mM, pH7.5; $PBR_{322}$ supercoiled double stranded circular DNA (4363 base pairs, from Bochringer Mannheim Biochemicals) 0.125 µg/ml, drug (camptothecin or its derivatives) concentration at 1, 10 and 100 µM, in the presence of purified DNA topoisomerase I with final volume of 20 µl as described previously. Hsiang, Y. H., et al., "Camptothecin Induces Protein-Linked DNA Breaks Via Mammalian DNA Topoisomerase I," J. Biol. Chem., 260, 14873 (1985), the disclosure of which is incorporated herein by reference. Incubation was carried out at 37° C. for 60 min. The reaction was stopped by adding the loading buffer dye (2% sodium dodesyl sulfate, 0.05% bromophenol blue and 6% glycerol). Electrophoresis was carried cut on 1% agarose gel plus ethidium bromide (1 µg/ml) in TBE buffer (Tris-base-boric acid-EDTA) and ran at 25 V for 18 hrs. Photographs were taken under UV light using Polaroid film type 55/N and developed as indicated by the manufacturer.

Inhibition of Topo I Mediated Relaxation of Supercoiled DNA

To study the inhibiting effect on DNA topoisomerase I mediated relaxation of DNA, the method described by Liu and Miller was used. Liu, H. F. et al., "Cleavage of DNA by Mammalian DNA Topoisomerase II," *J. Biol. Chem.*, 258, 15365 (1980), the disclosure of which is incorporated herein by reference. For this assay, 0.18 μg of $PBR_{322}$ DNA, 0.5 U of Topo I (GIBCO-BRL), various concentrations (1–100 μM of camptothecin or an analog, in a reaction mixture (20 μl) containing 50 mM Tris-HCl, pH 7.5, 120 mM KCl, 10 mM $MgCl_2$, 0.5 mM DTT, 0.5 mM EDTA, 30 μg/ml BSA, 20 μg/ml $PBR_{322}$ DNA and various amounts of the enzyme was incubated at 37° C. for 30 min., and stopped with 5% SBS and 150 μg/ml proteinase K. The samples were loaded onto 1% agarose in TAE running buffer, electrophoresed overnight at 39 V, stained with EtBr, and photographed under UV light.

Antitumor Activity in vivo

Antitumor activities of camptothecin derivatives were tested in $B_6D_2F_1$ mice bearing sarcoma-180 or Lewis lung murine solid tumor. For S-180, 3×106 cells were innoculated subcutaneously on day 3. Antitumor treatment started on day 1 intraperitoneally twice daily for five days. Tumor volumes on day 7 and day 14 were measured. Average tumor volumes were described as the ratio of treated versus untreated control (T/C). The control (treated with DMSO vehicle only) tumor volumes for day 7 and day 14 were 0.11 $cm^3$ and 0.61 $cm^3$, respectively. The T/C camptothecin is designated with "+++." An increment or decrement of 10% as compared to the camptothecin T/C on day 14 at 2 mg/kg dosage is designated with increase or decrease of one "+" unit, respectively.

For Lewis lung carcinoma, tumor cells (1×106) were inoculated subcutaneously on day 0 and treatment started on day 1, intraperitoneally twice daily for five days. The grading of effects was as described above.

As shown Table 1, many of the camptothecin derivatives tested for the antitumor cytotoxicity in vitro exhibited higher potency than camptothecin in one to three cell lines. Most of those compounds exhibiting higher antitumor cytotoxicity also exhibited higher potency in enhancing the DNA-topoisomerase I-mediated cleavage of $PBR_{322}$ DNA, or in inhibiting the DNA-topoisomerase I-mediated relaxation of $PBR_{322}$ DNA. These results suggest excellent correlation between the antitumor cytoxicity of the camptothecin compounds with their ability to inhibit the functions of DNA-topoisomerase I.

For in vivo chemotherapeutic effects in tumor-bearing mice, for example, 7-trimethylsilyl camptothecin showed better activity than camptothecin against sarcoma 180 in $B_6D_2F_1$ mice at several equivalent doses in a dose dependent manner in terms of tumor volume reduction. Similarly, for Lewis lung carcinoma, 7-trimethylsilyl-11-flouro camptothecin exhibited a similar antitumor effect to camptothecin in terms of tumor volume reduction at 4-fold lower doses than camptothecin. Thus, 7-trimethylsilyl-11-flouro camptothecin is more efficacious than camptothecin in its antitumor effects in vivo.

The present inventors have thus discovered that introduction of a silyl group (for example, a trimethylsilyl group) at position 7 of the camptothecin structure typically results in a compound with better anti-tumor activity than camptothecin (see, for example, the compound of Example 1 as compared to (20S)-CPT). The silyl group is also beneficial in the irinotecan series (see, for example, the compound of Example 6 as compared to irinotecan).

The anti-tumor activity remains essentially unchanged when a hydroxy group is introduced at position 10 of the compound of Example 1 to produce the compound of Example 5. The compound of Example 6 is a relative of SN-38, the active metabolite of irinotecan. Some of the highest activities were observed in the present studies when a trimethylsilyl group was introduced in conjunction with a fluoro atom at position 11 (see, for example, the compound of Example 7), or a primary amine group at positions 10 or 11 (see, respectively, Examples 8 and 9). Introduction of a fluoro atom in position 12 also results in an analog only approximately 2 times less potent than camptothecin (see, Example 11 as compared to (20S)-CPT). This result is surprising considering the poor activity of the 12-substituted camptothecins reported previously in the literature.

A mammal (human or animal) may thus be treated by a method which comprises the administration to the mammal of a pharmaceutically effective amount of a compound of formula (1) or a pharmaceutically acceptable salt thereof. The condition of the mammal can thereby be improved.

The compounds of the present invention can be administered in a variety of dosage forms including, for example: parenterally (for example, intravenously, intradermally, intramuscularly or subcutaneously); orally (for example, in the form of tablets, lozengers, capsules, suspensions or liquid solutions); rectally or vaginally, in the form of a suppository; or topically (for example, as a paste, cream, gel or lotion).

Optimal dosages to be administered may be determined by those skilled in the art and will vary with the particular compound of formula (1) to be used, the strength of the preparation, the mode of administration, the time and frequency of administration, and the advancement of the patient's condition. Additional factors depending on the particular patient will result in the need to adjust dosages. Such factors include patient age, weight, gender and diet. Dosages may be administered at once or divided into a number of smaller doses administered at varying intervals of time.

EXAMPLES

The following examples are provided for illustration of the invention and are not intended to be limiting thereof.

Example 1

Preparation of (20S)-7-trimethylsilylcamptothecin

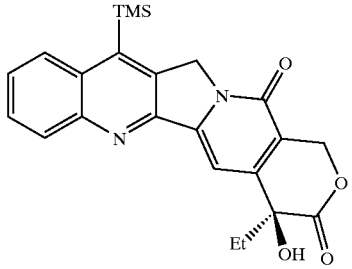

(1) (S)-4-Ethyl-4-hydroxy-6-iodo-3-oxo-7-(3-trimethylsilyl-2-propynyl)-1H-pyrano[3,4-c]-8-pyridone To a solution of (S)-4-ethyl-4-hydroxy-6-iodo-3-oxo -1H-pyrano[3,4-c]-8-pyridone [iodopyridone (2), 250 mg, 0.746 mmol]in DME (2.5 mL) and DMF (0.60 mL) at 0° C. under argon was added 60% NaH in mineral oil (31.3 mg, 0.783 mmol). LiBr (150 mg, 1.75 mmol) was added 10 min latter. After 15 min at room temperature, 3-trimethylsilyl-2- propynyl bromide (430 mg, 2.24 mmol) was injected and the reaction mixture was heated in the dark at 65° C. for 20 h. The final solution was poured into brine (20 mL), extracted with AcOEt (6×15 mL) and dried ($Na_2SO_4$). The residue obtained after removal of the solvents was subjected to flash-chromatography ($CHCl_3$/AcOEt 95:5) to give 283 mg (85%) of a foam: $[\alpha]^{20}_D$+36.7 (c 1, $CHCl_3$); IR (neat, $cm^{-1}$) 3384, 2940, 2166, 1730, 1634, 1518, 1406, 1130, 841, 752; $^1$H NMR (300 MHz, $CDCl_3$) δ0.14 (s, 9H), 0.95 (t, J=7.4 Hz, 3H), 1.77 (m, 2H), 3.66 (s, 1H), 5.00 (d, J=17.2 Hz, 1H), 5.10 (d, J=16.4 Hz, 1H), 5.15 (d, J=17.2 Hz, 1H), 5.49 (d, J=16.4 Hz, 1H), 7.16 (s, 1H); $^{13}$C NMR (75 MHz, $CDCl_3$) δ−0.40, 7.7, 31.5, 44.5, 66.3, 71.8, 90.9, 97.9, 116.5, 118.1, 148.6, 157.9, 173.3; HRMS (EI) m/z calcd for $C_{16}H_{20}INO_4Si$ ($M^+$) 445.0206, found 445.0203; LRMS (EI) m/z 445 ($M^+$), 430, 416, 386.

(2) (20S)-7-Trimethylsilylcamptothecin

A solution of the compound prepared in (1) (36.6 mg, 0.082 mmol), phenyl isonitrile (0.25 mmol) and hexamethylditin (42 mg, 0.123 mmol) in benzene (1.3 mL) under argon was irradiated at 70° C. with a 275 W GE sunlamp for 10 h. The final reaction mixture was concentrated and subjected to flash-chromatography ($CHCl_3$/MeOH 96:4) to provide 18.8 mg (54%) of a slightly yellow solid: $[\alpha]^{20}_D$ +39.0 (c 0.2, $CHCl_3$/MeOH 4:1); $^1$H NMR (300 MHz, $CDCl_{13}$/$CD_3OD$ 3:1) δ0.50 (s, 9H), 0.83 (t, J=7.4 Hz, 3H), 1.74 (m, 2H), 3.72 (br s, 1H), 5.12 (d, J=16.4 Hz, 1H), 5.16 (br s, 2H), 5.47 (d, J=16.4 Hz, 1H), 7.49 (t, J=8.1 Hz, 1H), 7.54 (s, 1H), 7.62 (t, J=8.1 Hz, 1H), 8.02 (d, J=8.1 Hz, 1H), 8.07 (d, J=8.1 Hz, 1H); $^{13}$C NMR (75 MHz, $CDCl_{13}$/$CD_3OD$ 3:1) δ0.9, 7.2, 29.3, 31.0, 51.7, 65.5, 98.3, 118.4, 127.3, 128.0, 129.7, 130.0, 131.8, 134.3, 144.7, 145.6, 147.3, 151.1, 173.5; HRMS (EI) m/z calcd for $C_{23}H_{24}N_2O_4Si$ ($M^+$) 420.1505, found 420.1501; LRMS (EI) m/z 420 ($M^+$), 391, 376, 361, 347, 320, 291.

Example 2

Preparation of (20S)-7-tert-butyldimethylsilylcamptothecin

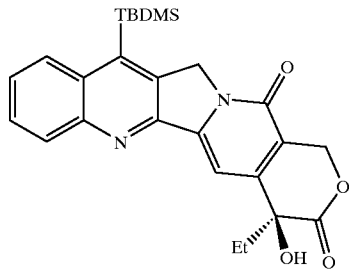

(1) (S)-4-Ethyl-4-hydroxy-6-iodo-3-oxo-7-(3-tert-butyldimethylsilyl -2-propynyl)-1H-pyrano[3,4-c]-8-pyridone Following the procedure described in Example 1-(1), iodopyridone (2) (200 mg, 0.60 mmol) and 3-tert-butyldimethylsilyl -2-propynyl bromide (280 mg, 1.20 mmol) provided, after flash-chromatography ($CH_2Cl_2$/AcOEt 9:1), 173 mg (59%) of a white foam: $[\alpha]^{20}_D$+58 (c 0.2, $CHCl_3$); IR ($CHCl_3$, $cm^{-1}$) 3548, 2950, 2927, 2859, 1745, 1648, 1526; $^1$H NMR (300 MHz, $CDCl_3$) δ0.08 (s, 6H), 0.92 (m, 12H), 1.79 (m, 2H), 3.77 (br s, 1H), 5.00–5.25 (m, 3H), 5.50 (d, J =16.4 Hz, 1H) 7.19 (s, 1H); $^{13}$C NMR (75 MHz, $CDCl_3$)δ−4.9, 7.63, 16.6, 26.0, 31.6, 44.5, 66.3, 71.8, 89.4, 98.6, 100.0, 116.5, 118.1, 148.6, 158.0, 173.2; HRMS (EI) m/z calcd for $C_{19}H_{26}INO_4Si$ ($M^+$) 487.0679, found 487.0676; LRMS (EI) m/z 487 ($M^+$), 430, 386, 96, 81, 57.

(2) (20S)-7-tert-butyldimethylsilylcamptothecin

Following the procedure described in Example 1-(2), the compound prepared in (1) (48.7 mg, 0.10 mmol) afforded, after flash-chromatographies ($CH_2Cl_2$/MeOH 96:4; $CH_2Cl_2$/acetone 9:1), 24.8 mg (54%) of an off yellow solid: $[\alpha]^{20}_D$+ 35.5 (c 0.2, $CHCl_3$); IR ($CHCl_3$, $cm^{-1}$) 3028, 2980, 2960, 2932, 2859, 1741, 1658, 1600, 1555, 1257, 1198, 1158, 1045; $^1$H NMR (300 MHz, $CDCl_3$) δ0.69 (s, 6H), 0.98 (s, 9H), 1.03 (t, J=7.3 Hz, 3H), 1.86 (m, 2H), 3.86 (s, 1H), 5.29 (d, J=16.3 Hz, 1H), 5.31 (s, 2H), 5.73 (d, J=16.3 Hz, 1H), 7.60 (t, J=6.3 Hz, 1H), 7.60 (t, J=7.0 Hz, 1H), 7.66 (s, 1H), 7.74 (t, J=7.3 Hz, 1H) 8.20 (t, J=8.1 Hz, 2H); $^{13}$C NMR (75 MHz, $CDCl_3$) δ0.56, 7.80, 19.2, 27.1, 31.6, 52.4, 66.3, 72.8, 97.7, 118.2, 127.0, 129.5, 129.6, 130.8, 132.7, 136.0, 143.0, 146.4, 148.0, 150.1, 150.6, 157.4, 173.9; HRMS (EI) m/z calcd for $C_{26}H_{30}N_2O_4Si$ ($M^+$) 462.1974, found 462.1975; LRMS (EI) m/z 462 ($M^+$), 450, 361, 331, 304, 245, 223, 57.

Example 3

Preparation of (20S)-7-tert-butyldiphenylsilylcamptothecin

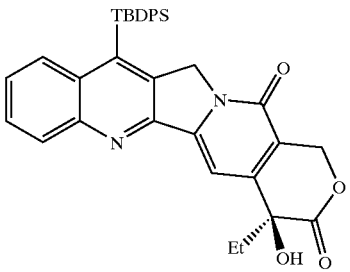

(1) (S)-4-Ethyl-4-hydroxy-6-iodo-3-oxo-7-(3-tert-butyldiphenylsilyl -2-propynyl)-1H-pyrano[3,4-c]-8-pyridone Following the procedure described in Example 1-(1), iodopyridone (2) (200 mg, 0.60 mmol) and 3-tert-butyldiphenylsilyl -2-propynyl bromide (428 mg, 1.20 mmol) provided, after flash-chromatography ($CH_2Cl_2$/AcOEt 9:1), 258 mg (70%) of a white foam: $[\alpha]^{20}_D$+45.1 (c 0.2, $CHCl_3$); IR ($CHCl_3$, $cm^{-1}$) 3546, 2928, 2855, 1741, 1658, 1526; $^1$H NMR (300 MHz, $CDCl_3$) δ0.97 (t, J=7.3 Hz, 3H), 1.08 (s, 9H), 1.80 (m, J=7.1 Hz, 2H), 3.76 (br s, 1H), 5.13 (d, J=16.4 Hz, 1H), 5.29 (d, J=2.5 Hz, 2H), 5.52 (d, J=16.4 Hz, 1H), 7.22 (s, 1H), 7.32–7.40 (m, 6H), 7.76–7.78 (m, 4H); $^{13}$C NMR (75 MHz, $CDCl_{13}$) δ7.6, 18.6, 27.0, 31.6, 44.6, 60.4, 66.3, 71.8, 86.5, 99.9, 102.2, 116.6, 127.7, 129.6, 132.6, 135.6, 148.7, 157.8, 173.2; HRMS (EI) m/z calcd for $C_{25}H_{21}INO_4Si$ ($M-C_4H_9^+$) 554.0279, found 554.0285; LRMS (EI) m/z 554 ($M-C_4H_9^+$), 587, 510, 220, 143, 105.

(2) (20S) -7-tert -butyldiphenylsilylcamptothecin

Following the procedure described in Example 1-(2), the compound prepared in (1) (61.1 mg, 0.10 mmol) yielded, after flash-chromatographies ($CH_2Cl_2$/MeOH 96:4; $CH_2Cl_2$/acetone 9:1), 26.5 mg (45%) of a light yellow solid: $[\alpha]^{20}_D$+ 35.2 (c 0.2, $CHCl_3$); IR ($CHCl_3$, $cm^{-1}$) 3003, 2984, 2969, 2958, 2935, 1741, 1658, 1599, 1555, 1428, 1226, 1216, 1158, 1102; $^1$H NMR (300 MHz, $CDCl_3$) δ1.00 (t, J=7.3 Hz, 3H), 1.44 (s, 9H), 1.84 (m, 2H), 3.75 (s, 1H), 4.21 (d, J=5.7 Hz, 2H), 5.19 (d, J=16.3 Hz, 1H), 5.64 (d, J=16.3 Hz, 1H), 7.43 (m, 5H), 7.51 (t, J=7.3 Hz, 2H), 7.62 (s, 1H), 7.69 (m, 5H), 8.10 (d, J=8.5 Hz, 1H), 8.22 (d, J=8.2 Hz, 1H); $^{13}$C NMR (75 MHz, $CDCl_3$) δ7.9, 20.4, 30.2, 31.6, 52.2, 66.4, 72.8, 97.5, 118.2, 126.3, 128.6, 129.8, 130.3, 130.7, 131.9, 132.2, 134.6, 134.64, 136.4, 136.5, 138.1, 140.9, 146.2, 148.4, 149.9, 151.3, 157.1, 174.1; HRMS (EI) m/z calcd for $C_{36}H_{34}N_2O_4Si$ ($M^+$) 586.2281, found 586.2288; LRMS (EI) m/z 586 ($M^+$), 542, 529, 485, 428, 407, 321, 181, 131, 69.

Example 4

Figure 3:
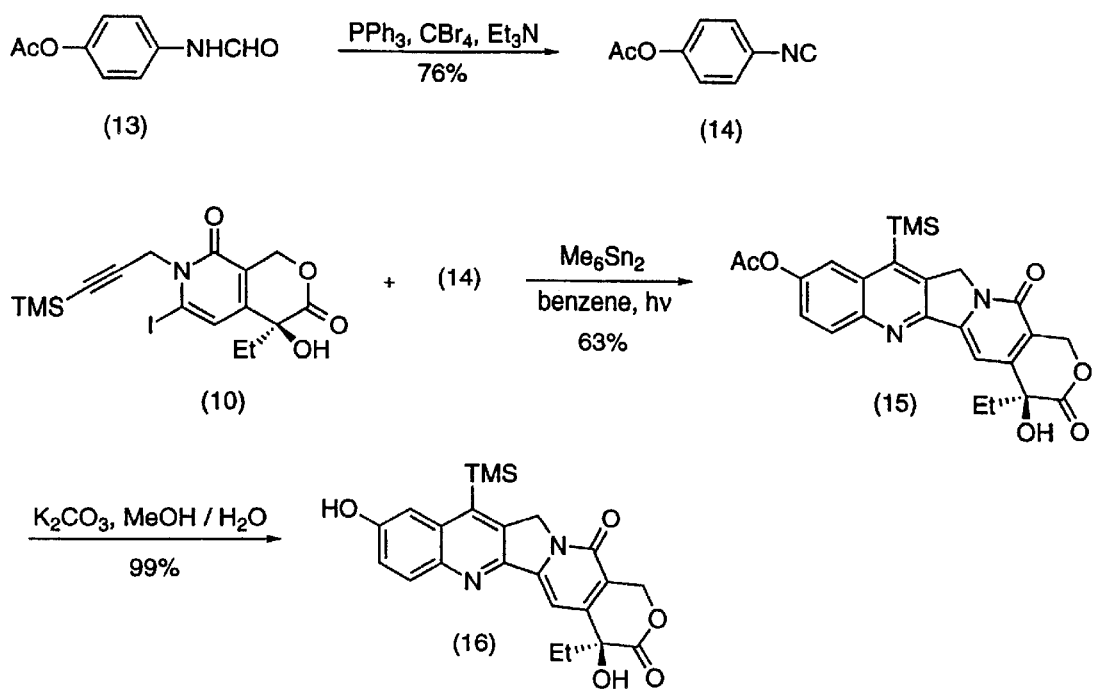
FIG. 3 is an illustration of a synthesis of (20S)-10-acetoxy-7-trimethylsilylcamptothecin and (20S)-10-hydroxy-7-trimethylsilylcamptothecin.

Preparation of (20S)-10-acetoxy-7-trimethylsilylcamptothecin (see FIG. 3)

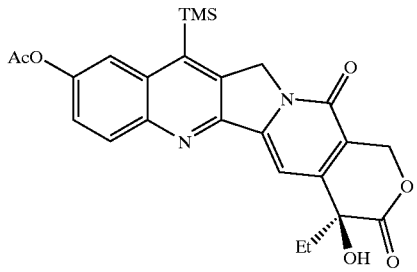

(1) 4-Acetoxyphenyl isonitrile (14)

To a solution of 4-acetoxyformanilide (13) (358 mg, 1.0 mmol) in $CH_2Cl_2$ (10 mL) at 0° C. were successively added tetrabromomethane (0.70 g, 2.1 mmol), triphenylphosphine (525 mg, 2.1 mmol), and triethylamine (320 mL, 2.1 mmol), and the resulting mixture was refluxed in the dark for 3 h. After evaporation of the solvents, the crude was triturated in ice-cooled $Et_2O$ (20 mL) and filtered. The solvent was evaporated and the residue was purified by flash-chromatography (hexanes/AcOEt 8:2) to afford 243 mg (76%) of a slightly brown solid: IR (neat, $cm^{-1}$) 2127, 1768, 1501, 1370, 1201, 1180, 909; $^1H$ NMR (300 MHz, $CDCl_3$) δ2.29 (s, 3H), 7.11 (d, J=8.8 Hz, 2H), 7.38 (d, J=8.8 Hz, 2H); $^{13}C$ NMR (75 MHz, $CDCl_3$) δ21.0, 122.8, 127.6, 150.8, 164.3, 168.8; HRMS (EI) m/z calcd for $C_9H_7NO_2$ ($M^+$) 161.0477, found 161.0474; LRMS (EI) m/z 161 ($M^+$), 133, 119, 91.

(2) (20S)-10-Acetoxy-7-trimethylsilylcamptothecin (15)

Following the procedure described in Example 1-(2), the compound prepared in Example 1-(1) (44.5 mg, 0.10 mmol) and the compound prepared in (1) (48.3 mg, 0.30 mmol) provided, after flash-chromatography ($CHCl_3$/acetone 10:1), 29.9 mg (63%) of a slightly yellow oil: $[α]^{20}_D$ +29.9 (c 0.5, $CHCl_3$); $^1H$ NMR (300 MHz, $CDCl_3$) δ0.61 (s, 9H), 0.98 (t, J=7.4 Hz, 3H), 1.86 (m, 2H), 2.38 (s, 3H), 4.13 (br s, 1H), 5.24 (d, J=16.4 Hz, 1H), 5.27 (s, 2H), 5.68 (d, J=16.4 Hz, 1H), 7.46 (dd, J=9.2, 2.5 Hz, 1H), 7.60 (s, 1H), 7.96 (d, J=2.5 Hz, 1H), 8.13 (d, J=9.2 Hz, 1H); $^{13}C$ NMR (75 MHz, $CDCl_3$) δ1.4, 7.8, 21.4, 31.5, 51.7, 66.2, 97.6, 118.3, 118.9, 124.6, 132.1, 135.0, 145.7, 146.1, 148.9, 150.1, 150.7, 157.3, 169.1, 173.7; HRMS (EI) m/z calcd for $C_{25}H_{26}N_2O_6Si$ ($M^+$) 478.1560, found 478.1582; LRMS (EI) m/z 478 ($M^+$), 436, 392, 377, 336, 277.

Example 5

Preparation of (20S)-10-hydroxy-7-trimethylsilylcamptothecin (16)

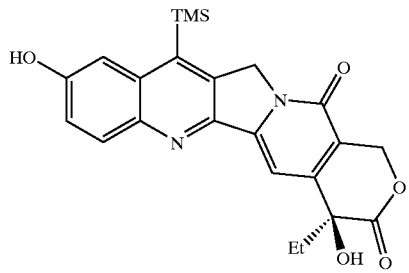

A solution of the compound (15) prepared in Example 5-(2) (16.8 mg, 0.035 mmol) and $K_2CO_3$ (9.6 mg, 0.070 mmol in MeOH (100 mL) and $H_2O$ (100 mL) was stirred 1 h 30 at room temperature. The reaction mixture was acidified with ACOH (2 drops), diluted with brine (10 mL) and extracted with AcOEt (10×10 mL). The combined organic layers were dried ($Na_2SO_4$) and evaporated, and the residue was purified by flash-chromatographies ($CHCl_3$/MeOH/AcOH 90:10:2; $CHCl_3$/acetone 2:1) to give 15.1 mg (99%) of a white solid: $[α]^{20}_D$ +18.9 (c 0.2, $CHCl_3$/MeOH 4:1); $^1H$ NMR (300 MHz, $CDCl_3$/$CD_3OD$ 4:1) δ0.45 (s, 9H), 0.84 (t, J=7.3 Hz, 3H), 1.75 (m, 2H), 5.12 (br s, 2H), 5.12 (d, J=16.3 Hz, 1H), 5.48 (d, J=16.3 Hz, 1H), 7.24 (dd, J=9.1, 2.5 Hz, 1H), 7.39 (d, J=2.5 Hz, 1H), 7.87 (d, J=9.1 Hz, 1H); $^{13}C$ NMR (75 MHz, $CDCl_3$/$CD_3OD$ 4:1) δ0.8, 7.4, 31.1, 51.8, 65.7, 97.5, 109.8, 117.5, 122.3, 131.3, 133.7, 134.6, 141.7, 142.6, 146.3, 147.5, 151.1, 156.3, 157.6; HRMS (EI) m/z calcd for $C_{23}H_{24}N_2O_5Si$ ($M^+$) 436.1454, found 436.1450; LRMS (EI) m/z 436 ($M^+$), 392, 377, 336, 323.

Reaction of this compound with $NH_2CH_2CH_2NMe_2$ followed by EtCOCl provided the open E-ring analog for biological testing.

Example 6

Figure 6:
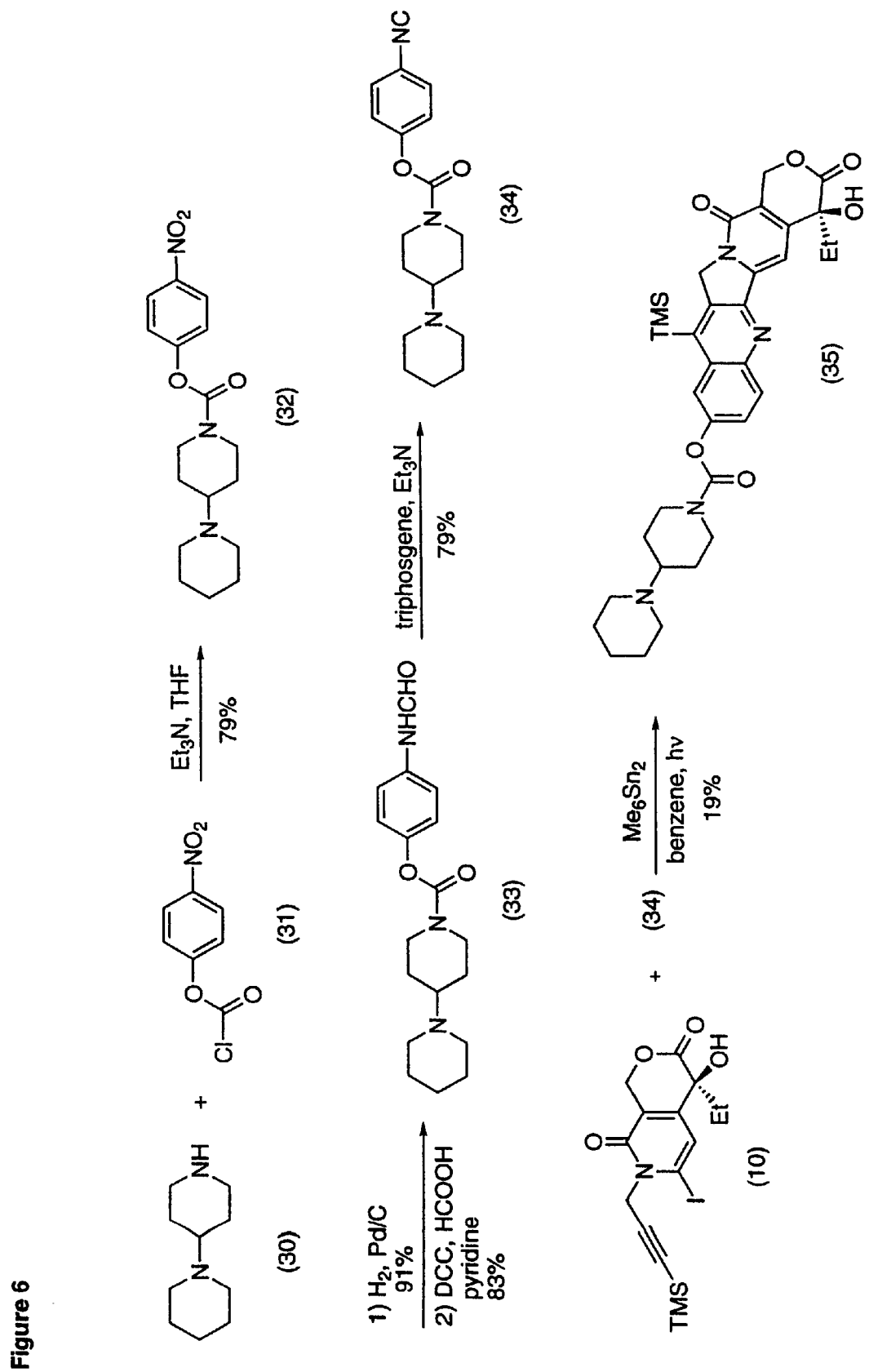
FIG. 6 is an illustration of a synthesis of a novel analog of irinotecan.

Preparation of (20S) 7-trimethylsilyl-irinotecan (see FIG. 6)

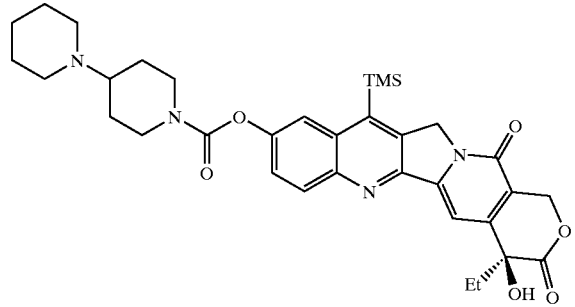

(1) [1,4'] Bipiperidinyl-1'-carboxylic acid 4-nitrophenylester (32)

To a solution of 4-nitrophenyl chloroformate (31) (5.15 g, 25.6 mmol) in 150 mL of dry THF at −78° C. was added triethylamine (10.7 mL, 76.2 mmol), followed by a solution of 4-piperidinopiperidine (30) (4.51 g, 25.6 mmol) in 40 mL of THF. This solution was stirred for two hours, after which the solvent was removed, and the residue was taken up in AcOEt, filtered and evaporated. The crude yellow solid was passed through a pad of neutral alumina using AcOEt as an eluent to yield, after evaporation, 6.73 g (79%) of a white solid: IR ($CHCl_3$, $cm^{-1}$) 3046, 2937, 2859, 1704, 1620, 1513, 1466, 1242, 1197; $^1H$ NMR (300 MHz, $CDCl_3$) δ1.20–1.80 (m, 8H), 1.90 (d, J=12.7 Hz, 2H), 2.20–2.70 (m, 5H), 2. 87 (t, J=12 Hz , 1H), 3. 01 (t, J=12 Hz, 1H) 4. 30 (br s, 2H), 7.29 (d, J=9 Hz, 2H), 8.26 (d, J=9 Hz, 2H); $^{13}C$ NMR (75 MHz, $CDCl_3$) δ24.6, 26.3, 27.5, 28.2, 40.1, 44.4, 50.1, 62.0, 122.2, 124.9, 144.8, 151.9, 156.3; HRMS (EI) m/z calcd for $C_{17}H_{23}N_3O_4$ ($M^+$) 333.1676, found 333.1688; LRMS (EI) m/z 333 ($M^+$), 195, 167, 124, 110, 96, 55.

(2) [1,4'] Bipiperidinyl-1'-carboxylic acid 4-aminophenylester

To a solution of the compound prepared in (1) (1.012 g, 3.03 mmol) in AcOEt (125 ml) was added 10% Pd/C (0.15 g). The system was purged several times with argon, and a 1 L balloon of $H_2$ was added. After stirring the resulting mixture at room temperature for 12 hours, the catalyst was removed by filtration through celite and the solvent was evaporated to give 835 mg (91%) of a white solid: IR ($CHCl_3$, $cm^{-1}$) 3453, 3400, 3028, 2936, 2859, 1703, 1513, 1429, 1242, 1226, 1210, 1197; $^1$H NMR (300 MHz, CDCl$_3$) δ1.30–1.70 (m, 8H), 1.86 (d, J=12.6 Hz, 2H), 2.33–2.62 (m, 5H), 2.68–3.04 (m, 2H), 3.58 (br s, 2H), 4.30 (br s, 2H), 6.64 (d, J=6.0 Hz, 2H), 6.87 (d, J=6.0 Hz, 2H); $^{13}$C NMR (75 MHz, CDCl$_3$) δ24.6, 26.3, 27.5, 28.1, 43.8, 43.9, 50.1, 62.3, 115.4, 122.3, 143.4, 143.7, 154.1; HRMS (EI) m/z calcd for C$_{17}$H$_{25}$N$_3$O$_2$ (M$^+$) 303.1944, found 303.1947; LRMS (EI) m/z 303 (M$^+$), 195, 167, 124, 108, 96, 80, 65, 55.

(3) [1,4'] Bipiperidinyl-1'-carboxylic acid 4-formylaminophenylester (33)

To a stirred solution of dicyclohexylcarbodiimide (272 mg, 1.32 mmol) in CH$_2$Cl$_2$ (5 mL) at 0° C. was added 98% formic acid (60.7 mg, 1.32 mmol) dropwise. After 10 minutes, the resulting mixture was added via syringe to a solution of the compound prepared in Example (2) (200 mg, 0.66 mmol) in pyridine (5 mL) at 0° C. The reaction mixture was then allowed to warm to room temperature and stirred 3 h. The pyridine solvent was evaporated and the residue was taken up in CH$_2$Cl$_2$, filtered, evaporated and subjected directly to a basic alumina column (CH$_2$Cl$_2$/MeOH 95:5) to give 118 mg (83%) of a white solid, which consists, at room temperature, of a mixture of the cis and trans rotamers originating from hindered rotation around the formamide carbon-nitrogen bond: IR (CHCl$_3$, cm$^{-1}$) 3025, 3013, 2937, 2888, 2861, 1703, 1517, 1466, 1275, 1226, 1210; $^1$H NMR (300 MHz, CDCl$_3$) δ1.38–1.80 (m, 8H), 1.90 (d, J=12 Hz, 2H), 2.40–2.70 (m, 5H), 2.83 (t, J=12 Hz, 1H), 2.97 (t, J=12 Hz, 1H), 4.32 (m, 2H), 7.03–7.11 (m, 3H), 7.37 (br s, 0.5H) (cis), 7.46 (d, J=10 Hz, 1H), 7.53 (d, J=11 Hz, 0.5H) (trans), 8.32 (d, J=2 Hz, 0.5H) (cis), 8.59 (d, J=11 Hz, 0.5H) (trans); $^{13}$C NMR (75 MHz, CDCl$_3$) δ24.6, 26.3, 27.6, 28.1, 44.2, 44.0, 50.1, 82.2, 120.0, 121.0, 122.1, 123.0, 133.9, 134.3, 147.5, 148.9, 153.9, 153.4, 159.1, 162.5; HRMS (EI) m/z calcd for C$_{18}$H$_{25}$N$_3$O$_3$ (M$^+$) 331.1884, found 331.1896; LRMS (EI) m/z 331 (M$^+$), 244, 202, 167, 124, 80, 55.

(4) [1,4'] Bipiperidinyl-1'-carboxylic acid 4-isonitrilophenylester (34)

To a solution of the compound prepared in Example (3) (90.1 mg, 0.272 mmol) in CH$_2$Cl$_2$ (10 mL) were successively added triethylamine (69.5: mg, 0.688 mmol) them dropwise, at 0° C., a solution of triphosgene (68 mg, 0.229 mmol in dry CH$_2$Cl$_2$ (10 mL). The mixture was stirred 2 hours at room temperature, washed with 7% NaHCO$_3$ (5 mL) and dried (MgSO$_4$). The crude brown residue obtained after evaporation of the solvent was subjected to flash-chromatography (Et$_2$O/Et$_2$NH 95:5) to yield 67.2 mg (79%) of a white solid: IR (CHCl$_3$, cm$^{-1}$) 3034, 2937, 2131, 1718, 1504, 1429, 1233, 1224, 1213, 1198, 1184; $^1$H NMR (300 MHz, CDCl$_3$) δ1.32–1.75 (m, 8H), 1.90 (br d, J=12.4 Hz, 2H), 2.32–2.65 (m, 5H), 2.84 (t, J=12.3 Hz, 1H), 2.98 (t, J=12.1 Hz, 1H), 4.20–4.40 (m, 2H), 7.14 (d, J=8.8 Hz, 2H), 7.37 (d, J=8.8 Hz, 2H); $^{13}$C NMR (75 MHz, CDCl$_3$) δ25.0, 26.5, 27.8, 28.5, 44.4, 50.6, 62.7, 123.3, 127.8, 152.1, 153.1, 164.4; HRMS (EI) m/z calcd for C$_{18}$H$_{23}$N$_3$O$_2$ (M$^+$) 313.1779, found 313.1790; LRMS (EI) m/z 313 (M$^+$), 195, 167, 124, 110, 84, 55.

(5) (20S)-7-Trimethylsilyl-Irinotecan (35)

Following the procedure described in Example 1-(2), the compound prepared in Example 1-(1) (44.5 mg, 0.10 mmol), the compound prepared in (4) (93.9 mg,0.3 mmol), and hexamethylditin (50 mg, 0.15 mmol) in dry benzene (1.5 mL) were irradiated for 9 hours at 70° with a 275 W GE sunlamp. The reaction was evaporated, dissolved in MeOH with a few drops of DMSO to aid solubility and injected into a Waters reverse phase HPLC. The conditions used to effect separation were as follows. A Waters 600E system controller with a Waters 490E Programmable multiwavelength detector, a Sargent Welch plotter and Waters C-18 25×10 cartridge columns were employed. A gradient elution, [5:95 MeCN/H$_2$O (0.1% TFA) to 30:70 MeCN/H$_2$O (0.1% TFA)], over 40 minutes time at 20 mL/min gave a semipurified grey solid after lyophilization. The grey solid was further purified (CH$_2$Cl$_2$/EtOH 70:30) on a chromatotron using a 1 mm plate to give 12 mg (19%) of a yellow solid: [α]$^{20}_D$ +14.8 (c 0.2, CHCl$_3$); IR (CHCl$_3$, cm$^{-1}$) 3023, 2957, 2933, 1720, 1659, 1601, 1216, 1191, 1175, 1158; $^1$H NMR (300 MHz, CDCl$_3$) δ0.64 (s, 9H), 1.03 (t, J=7.3 Hz, 3H), 1.50–1.51 (br m, 2H), 1.51–1.52 (br m, 6H), 1.84 (m, J=7.3 Hz, 2H), 2.01–2.10 (br m, 2H), 2.60–2.75 (br s, 5H), 2.75–3.12 (br m, 2H), 4.30–4.50 (br m, 2H), 5.30 (d, J=16.3 Hz, 1H), 5.31 (s, 2H), 5.74 (d, J=16.3 Hz, 1H), 7.55 (dd, J=9.0, 2.4 Hz, 1H), 7.63 (s, 1H), 8.01 (d, J=2.3 Hz, 1H), 8.19 (d, J=9 Hz, 1H); $^{13}$C NMR (75 MHz, CDCl$_3$) δ1.5, 7.8, 25.4, 29.7, 31.5, 43.8, 50.1, 51.8, 62.5, 66.3, 72.8, 97.5, 118.1, 119.0, 125.1, 132.0, 132.3, 134.9, 143.4, 145.6, 146.4, 150.1, 150.5, 152.8, 157.4, 174.0; HRMS (EI) m/z calcd for C$_{34}$H$_{42}$N$_4$O$_6$Si (M$^+$) 630.2898, found 630.2874; LRMS (EI) m/z 630 (M$^+$), 586, 501, 457, 195, 167, 153, 124, 111, 96, 84.

Example 7

Preparation of (20S)-11-fluoro-7-trimethylsilylcamptothecin (see FIG. 2)

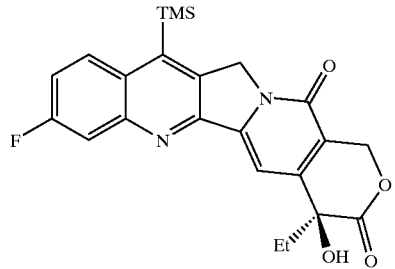

(1) 3-Fluoro-2-trimethylsilylbenzaldehyde (7)

The preparation of 3-fluoro-2-trimethylsilylbenzaldehyde proceeds through a selective ortho-metallation. See Comins, D. L. et al., J. Org. Chem., 49, 1078 (1984). See also Snieckus, V., Chem. Rev., 90, 879 (1990). To a solution of N,N,N'-trimethylethylenediamine (2.70 mL, 20 mmol) in THF (50 mL) was slowly added 1.6 N n-BuLi in hexanes (13 mL, 21 mmol) at −20° C., followed by 3-fluorobenzaldehyde (2.10 mL, 20 mmol) 15 min latter. After 15 minute at this temperature, 1.6 N n-BuLi in hexanes (38 mL, 60 mmol) was injected and the solution was stirred 1 h 30 at −35° C. Chlorotrimethylsilane (15 mL, 120 mmol) was added and the reaction mixture was stirred overnight at room temperature. The final solution was poured into ice-cooled 1 N HCl (150 mL), quickly extracted with Et$_2$O (3×100), washed with brine and dried (Na$_2$SO$_4$). After evaporation of the solvents, the residue was purified by flash-chromatography (hexanes/AcOEt 95:5) to provide 3.25 g (83%) of an oil: IR (neat, cm$^{-1}$) 1701, 1440, 1252, 1233, 1109, 848, 764; $^1$H NMR (300 MHz, CDC13) δ0.40 (d, J=2.6 Hz, 9H), 7.18 (br t, J=9.0 Hz, 1H), 7.47 (ddd, J$_1$=J$_2$=8.1 Hz, J$_3$=5.4 Hz, 1H), 7.70 (br d, J=7.5 Hz, 1H); $^{13}$C NMR (75 MHz, CDCl$_3$) δ1.8, 120.8 (d, J$_{CF}$=29 Hz), 126.8, 128.2, 131.2, 143.3, 167.6 (d, J$_{CF}$=244 Hz), 192.4; HRMS (EI) m/z calcd for C$_9$H$_{10}$OFOSi (M—CH$_3^+$) 181.0485, found 181.0482; LRMS (EI) m/z 181 (M—CH$_3^+$), 151, 125, 103, 91.

(2) 3-Fluoro-2-trimethylsilylbenzoic acid

A classical oxidation to the free acid was then performed. See Hill, L. R. et al., J. Org. Chem., 50, 470 (1985). To a solution of the compound prepared in (1) (3.41 g, 17.3 mmol) in tert-butanol (20 mL) were successively added a 2 N solution of 2-methyl-2-butene in THF (55 mL, 110 mmol) then slowly, over a period of 10 minutes, a solution of 80% $NaClO_2$ (2.55 g, 22.5 mmol) and $NaH_2PO_4 \cdot H_2O$ (3.10 g, 22.5 mmol) in water (18 mL). The resulting mixture was stirred 16 h at room temperature, the tert-butanol was evaporated, and the residue was taken up in 1 N NaOH (50 mL) and washed with hexanes (3×20 mL). The aqueous layer was acidified with 1 N HCl to pH 2, saturated with NaCl, and extracted with $Et_2O$ (3×50 mL). The combined organic layers were dried ($Na_2SO_4$) and evaporated to provide 3.13 g (85%) of a white solid: IR (NaCl, cm$^{-1}$) 2982, 1700, 1434, 1294, 1271, 1253, 1230, 849, 763; $^1$H NMR (300 MHz, CDCl$_3$) δ0.39 (d, J=2.6 Hz, 9H), 7.16 (br t, J=9.1 Hz, 1H), 7.41 (ddd, $J_1$=$J_2$=7.9 Hz, $J_3$=5.6 Hz, 1H), 7.73 (br d, J=7.7 Hz, 1H); $^{13}$C NMR (75 MHz, CDCl$_3$) δ1.3, 119.5 (d, JCF=27 Hz), 126.0, 127.3, 130.9, 138.0, 167.5 (d, JCF=243 Hz), 174.5; HRMS (EI) m/z calcd for $C_9H_{10}FO_2Si$ (M—CH$_3^+$) 197.0434, found 197.0433; LRMS (EI) m/z 197 (M—CH$_3^+$), 179, 133, 115, 105.

(3) 3-Fluoro-2-trimethylsilylphenyl isocyanate (8)

Preparation of the intermediate isocyanate was carried out via a Curtius rearrangement. See Capson, T. L. et al., *Tetrahedron Lett.*, 25, 3515 (1984) and references herein. To a solution of the compound prepared in (2) (3.03 g, 14.3 mmol) in $CH_2Cl_2$ (20 mL) was added oxalylchloride (1.30 mL, 15.0 mmol) and the resulting mixture was stirred 3 h at room temperature. The residue obtained after evaporation of the solvent was diluted with THF (10 mL) and injected with vigorous stirring to a ice-cooled solution of $NaN_3$ (3.70 g, 57 mmol) in $H_2O$ (20 mL) and acetone (50 mL). After 15 min at 0° C. and 1 min at room temperature, the solution was extracted with Et2O (4×50 mL) and dried ($Na_2SO_4$). The residue obtained after evaporation of solvents was refluxed in toluene for 1 h 30 to provide, upon solvent removal, 2.85 g (79%) of a slightly yellow oil: IR (neat, cm$^{-1}$) 2269, 1598, 1433, 1252, 1228, 846, 788; $^1$H NMR (300 MHz, CDCl$_3$) δ0.38 (d, J=1.9 Hz, 9H), 6.82 (br t, J=8.3 Hz, 1H), 6.90 (br d, J=8.2 Hz, 1H), 7.25 (ddd, $J_1$=$J_2$8.1 Hz, $J_3$6.6 Hz, 1H); $^{13}$C NMR (75 MHz, CDCl$_3$) δ0.4, 112.6 (d, $J_{CF}$=26Hz), 120.5, 122.5, 131.5, 139.2, 167.4 (d, $J_{CF}$241 Hz).

(4) 3-Fluoro-2-trimethylsilylphenyl isonitrile (9)

A deoxygenation then afforded the expected isonitrile. See Baldwin, J. E. et al., *Tetrahedron*, 39, 2989 (1983). Triethylamine (4.10 mL, 29.3 mmol) was added slowly at 0° C. to a 2 N solution of trichlorosilane in $CH_2Cl_2$ (8.40 mL, 16.8 mmol) followed, 5 min later, by the compound prepared in Example (3) (2.35 g. 11.2 mmol). After 1 h 30 at 0° C. and 30 min at room temperature, the solution was saturated with $NH_3$, filtered over Celite, washed with 5% $NaH_2PO_4$ and dried ($Na_2SO_4$). The crude obtained after evaporation of the solvent was then subjected to flash-chromatography (hexanes/AcOEt 95:5) to afford 1.42 g (66%) of a slightly purple liquid: IR (neat, cm$^{-1}$) 2114, 1598, 1440, 1254, 1237, 1110, 943, 848, 793; $^1$H NMR (300 MHz, CDCl$_3$) δ0.45 (d, J=1.8 Hz, 9H), 7.01. (br t, J=8.3 Hz, 1H), 7.17 (br d, J=7.7 Hz, 1H), 7.32 (ddd, $J_1$=$J_2$=8.0 Hz, $J_3$=6.1 Hz, 1H); $^{13}$C NMR (75 MHz, CDCl$_3$) δ0.1, 116.5 (d, $J_{CF}$=26 Hz), 124.3, 131.6, 166.8 (d, $J_{CF}$=243 Hz), 166.9; HRMS (EI) m/z calcd for $C_{10}H_{12}FNSi$ (M$^+$) 193.0723, found 193.0715; LRMS (EI) m/z 193 (M$^+$), 178, 150, 116, 105.

(5) (20S)-11-Fluoro-7,12-bis(trimethylsilyl)camptothecin (11)

Following the procedure described in Example 1-(2), the compound prepared in Example 1-(1) (43.5 mg, 0.098 mmol) and the compound prepared in Example (4) (76 mg, 0.39 mmol) provided, after flash-chromatography (CHCl$_3$/acetone 20:1), 33.4 mg (67%) of a slightly yellow oil: [α]$^{20}_D$ +23.6 (c 0.2, CHCl$_3$); $^1$H NMR (300 MHz, CDCl$_3$) δ0.53 (d, J=1.7 Hz, 9H), 0.60 (s, 9H), 1.02 (t, J=7.4 Hz, 3H), 1.88 (m, 2H), 3.82 (br s, 1H), 5.28 (d, J=16.3 Hz, 1H), 5.29 (br s, 2H), 5.72 (d, J=16.3 Hz, 1H), 7.31 (t, J=8.7 Hz, 1H), 7.46 (s, 1H), 8.18 (dd, J=9.2, 5.9 Hz, 1H); $^{13}$C NMR (75 MHz, CDCl$_3$) δ1.6, 1.7, 7.7, 31.4, 51.8, 66.3, 72.7, 97.2, 117.8 (d, $J_{CF}$=33 Hz), 124.3 (d, $J_{CF}$=28 Hz), 128.9, 131.1, 133.1, 144.4, 146.7, 150.1, 153.4, 157.4, 167.6 (d, $J_{CF}$=245 Hz), 173.9; HRMS (EI) m/z calcd for $C_{26}H_{31}FN_2O_4Si_2$ (M$^+$) 510.1806, found 510.1806; LRMS (EI) m/z 510 (M$^+$), 495, 466, 451, 395, 319.

(6) (20S)-11-Fluoro-7-trimethylsilylcamptothecin (12)

A solution of the compound prepared in Example (5) (19.5 mg, 0.038 mmol) in 48% HBr (1 mL) was heated at 50° C. for 20 h. The reaction mixture was slowly poured with vigorous stirring into saturated $NaHCO_3$ (10 mL), extracted with AcOEt (6×20 mL) and dried ($Na_2SO_4$). After evaporation of the solvent, the residue was purified by flash-chromatography (CHCl$_3$/acetone 8:1) to give 12.5 mg (83%) of a slightly yellow solid: [α]$^{20}_D$ +39.6 (c 0.2, CHCl$_3$); $^1$H NMR (300 MHz, CDCl$_3$) δ0.62 (s, 9H), 1.01 (t, J=7.4 Hz, 3H), 1.87 (m, 2H), 3.81 (br s, 1H), 5.28 (d, J=16.4 Hz, 1H), 5.28 (br s, 2H), 5.72 (d, J=16.4 Hz, 1H), 7.31 (ddd, J=9.6, 7.8, 2.8 Hz, 1H), 7.61 (s, 1H), 7.78 (dd, J=9.7, 2.7 Hz, 1H), 8.19 (dd, J=9.4, 5.8 Hz, 1H); $^{13}$C NMR (75 MHz, CDCl$_3$) δ1.6, 7.8, 31.5, 51.7, 66.3, 72.7, 97.8, 114.3 (d, $J_{CF}$=20 Hz), 117.7 (d, $J_{CF}$=26 Hz), 118.5, 128.9, 130.0, 133.9, 144.4, 146.1, 149.3, 150.1, 151.7, 157.4, 162.6 (d, $J_{CF}$=250 Hz), 173.9; HRMS (EI) m/z calcd for $C_{23}H_{23}FN_2O_4Si$ (M$^+$) 438.1411, found 438.1412; LRMS (EI) m/z 438 (M$^+$), 409, 394, 379, 365, 338, 309.

Example 8

Figure 4:
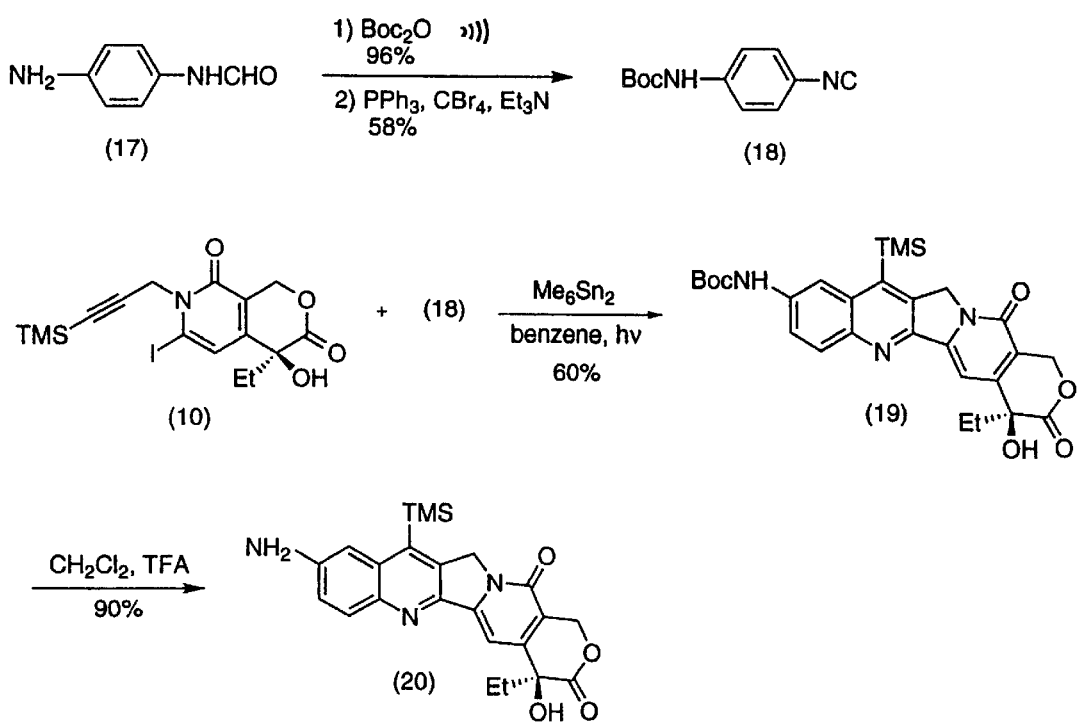
FIG. 4 is an illustration of a synthesis of (20S)-10-amino-7-trimethylsilylcamptothecin.

Preparation of (20S)-10-amino-7-trimethylsilylcamptothecin (see FIG. 4)

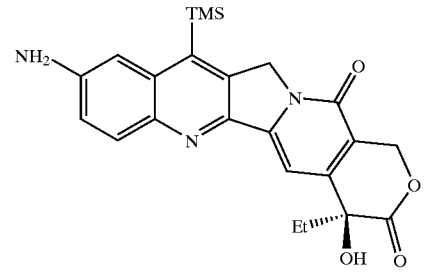

(1) 4-tert-Butyloxycarbonylaminophenyl isonitrile (18)

The isonitrile was prepared in 2 steps via classical Boc-protection followed by dehydration. See Einhorn, J. et al., *Synlett*, 37 (1991). A mixture of 4-aminoformanilide (1.71 g, 12.6 mmol), di-tert-butyl dicarbonate (2.87 g, 13.2 mmol) and $NaHCO_3$ (1.11 g, 13.2 mmol) in absolute EtOH (50 mL) was sonicated in a cleaning bath for 4 h. The final solution was filtered through a pad of Celite and concentrated to dryness. The residue was taken up in half brine (50 mL), extracted with AcOEt (6×30 mL) and dried ($Na_2SO_4$). After evaporation of the solvent, the residual oil was subjected to flash-chromatography (CHCl$_3$/MeOH 95:5) to give 2.85 g (96%) of 4-tert-butyloxycarbonylaminoformanilide, as a white solid. This intermediate (945 mg, 4.0 mmol) was subjected to the conditions described in Example 5-(1) to provide, after flash-chromatography (hexanes/AcOEt 9:1), 502 mg (58%) of a slightly brown solid: IR (NaCl, cm$^{-1}$) 3370, 2121, 1691, 1524, 1412, 1364, 1239, 1158, 832; $^1$H NMR (300 MHz, CDCl₃) δ1.48 (s, 9H), 6.75 (br s, 1H), 7.26 (d, J=8.8 Hz, 2H), 7.37 (d, J=8.8 Hz, 2H); ¹³C NMR (75 MHz, CDCl₃) δ28.2, 81.3, 118.5, 127.1, 139.4, 152.3, 162.7; HRMS (EI) m/z calcd for $C_{12}H_{14}N_2O_2$ (M⁺) 218.1055, found 218.1044; LRMS (EI) m/z 218 (M⁺), 162, 144.

(2) (20S)-10-tert-Butyloxycarbonylamino-7-trimethylsilyl camptothecin (19)

Following the procedure described in Example 1-(2), the compound prepared in Example 1-(1) (44.5 mg, 0.10 mmol) and the compound prepared in Example (1) (65 mg, 0.30 mmol) provided, after flash-chromatography (CHCl₃/acetone 6:1), 32.5 mg (60%) of a slighly yellow solid: $[\alpha]^2_D$ +28.0 (c 0.2, CHCl₃); ¹H NMR (300 MHz, CDCl₃) δ0.63 (s, 9H), 0.99 (t, J=7.4 Hz, 3H), 1.53 (s, 9H), 1.86 (m, 2H), 4.03 (br s, 1H), 5.24 (d, J=16.2 Hz, 1H), 5.26 (s, 2H), 5.70 (d, J=16.2 Hz, 1H), 7.00 (br s, 1H), 7.47 (dd, J=9.2, 2.3 Hz, 1H), 7.55 (s, 1H), 8.02 (d, J=9.2 Hz, 1H), 8.56 (br s, 1H); ¹³C NMR (75 MHz, CDCl₃) δ1.3, 7.8, 28.2, 31.5, 51.8, 66.3, 72.8, 97.1, 114.4, 117.8, 122.6, 131.3, 132.8, 135.0, 137.2, 142.9, 144.3, 146.6, 149.2, 150.1, 157.4, 173.9; HRMS (EI) m/z calcd for $C_{23}H_{25}N_3O_4Si$ (M-Boc⁺) 435.1614, found 435.1612; LRMS (EI) m/z 535 (M⁺), 479, 435, 391, 362, 335.

(3) (20S)-10-Amino-7-trimethylsilylcamptothecin (20)

A solution of the compound prepared in Example (2) (75.5 mg, 0.141 mmol) and TFA (500 mL) in CH₂Cl₂ (2 mL) was stirred 3 h at room temperature. The reaction mixture was then poured into saturated NaHCO₃ (50 mL), extracted with AcOEt (10×15 mL) and dried (Na₂SO₄). The residue obtained after evaporation of the solvents was purified by flash-chromatography (CHCl₃/MeOH 95:5) to afford 55.4 mg (90%) of a yellow solid: $[\alpha]^{20}_D$ +18.7 (c 0.15, CHCl₃/MeOH 4:1); ¹H NMR (300 MHz, CDCl₃/CD₃OD 4:1) δ0.40 (s, 9H), 0.80 (t, J=7.4 Hz, 3H), 1.70 (m, 2H), 5.05 (s, 2H), 5.08 (d, J=16.3 Hz, 1H), 5.43 (d, J=16.3 Hz, 1H), 7.05 (br s, 1H), 7.07 (d, J=8.0 Hz, 1H), 7.38 (s, 1H), 7.74 (d, J=8.0 Hz, 1H); ¹³C NMR (75 MHz, CDCl₃/CD₃OD 4:1) δ0.6, 7.2, 30.8, 51.8, 65.5, 72.7, 97.0, 107.2, 116.8, 122.0, 130.7, 134.0, 134.7, 139.9, 141.7, 145.8, 146.9, 151.2, 157.5, 173.7; HRMS (EI) m/z calcd for $C_{23}H_{25}N_3O_4Si$ (M⁺) 435.1614, found 435.1613; LRMS (EI) m/z 435 (M⁺), 391, 376, 335, 290.

Example 9
Preparation of (20S)-11-amino-7-trimethylsilylcamptothecin

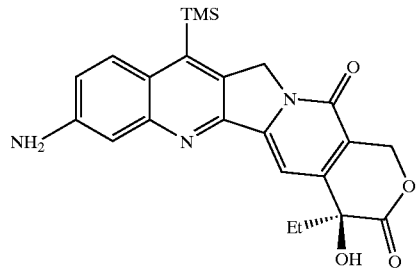

(1) 3-tert-Butyloxycarbonylaminophenyl isonitrile

The isonitrile was prepared in 2 steps following the same procedures as described in Example 9-(1). In the first step, the Boc-protection of 3-aminoformanilide (1.80 g 13.2 mmol) provided, after flash-chromatography-(CHCl₃/MeOH 95:5), 2.65 g (85%) of 3-tert-butyloxycarbonylaminoformanilide, as a white solid. This intermediate (412 mg, 1.74 mmol) was then subjected to the conditions described in Example 5-(1) to provide, after flash-chromatography (hexanes/AcOEt 9:1), 190 mg (50%) of a brown solid: IR (NaCl, cm⁻¹) 3318, 2126, 1715, 1603, 1547, 1433, 1236, 1162, 782; ¹H NMR (300 MHz, CDCl₃) δ1.49 (s, 9H), 6.67 (br s, 1H), 7.00 (m, 1H), 7.20–7.30 (m, 2H), 7.60 (br s, 1H); ¹³C NMR (75 MHz, CDCl₃) δ28.2, 81.3, 116.0, 118.9, 120.6, 129.8, 139.5, 152.3, 163.6; HRMS (EI) m/z calcd for $C_{12}H_{14}N_2O_2$ (M⁺) 218.1055, found 218.1047; LRMS (EI) m/z 218 (M⁺), 196, 162, 152, 118.

(2) (20S)-11-Amino-7-trimethylsilylcamptothecin

Following the procedure described in Example 1-(2), the compound prepared in Example 1-(l) (44.5 mg, 0.10 mmol) and the compound prepared in Example (1) (65.5 mg, 0.3 mmol) afforded, after flash-chromatographies (CHCl₃/MeOH 95:5; CHCl₃/acetone 5:1), 23.1 mg (43%) of a slighly yellow oil. This intermediate (14.7 mg, 0.027 mmol) was then deprotected following the conditions described in Example 9-(3) to provide, after flash-chromatography (CHCl₃/MeOH 9:1), 11.8 mg (99%) of (20S)-11-amino-7-trimethylsilylcamptothecin, as a yellow solid and with the exclusion of other isomers: $[\alpha]^{20}_D$ +15.0 (c 0.1, CHCl₃/MeOH 4:1); ¹H NMR (300 MHz, CDCl₃/CD₃OD 4:1) δ0.44 (s, 9H), 0.86 (t, J=7.4 Hz, 3H), 1.76 (m, 2H), 5.08 (s, 2H), 5.14 (d, J=16.4 Hz, 1H), 5.50 (d, J=16.3 Hz, 1H), 6.97 (dd, J=9.2, 2.5 Hz, 1H), 7.07 (d, J=2.5 Hz, 1H), 7.50 (s, 1H), 7.84 (d, J=9.2 Hz, 1H); ¹³C NMR (75 MHz, CDCl₃/CD₃OD 4:1) δ1.1, 7.4, 31.0, 51.7, 65.6, 97.9, 107.9, 117.8, 119.7, 125.9, 127.1, 129.0, 130.4, 135.4, 144.3, 149.5, 149.9, 151.1, 157.6, 175.3; HRMS (EI) m/z calcd for $C_{23}H_{25}N_3O_4Si$ (M⁺) 435.1614, found 435.1626; LRMS (EI) m/z 435 (M⁺), 406, 391, 376, 335.

Figure 5:
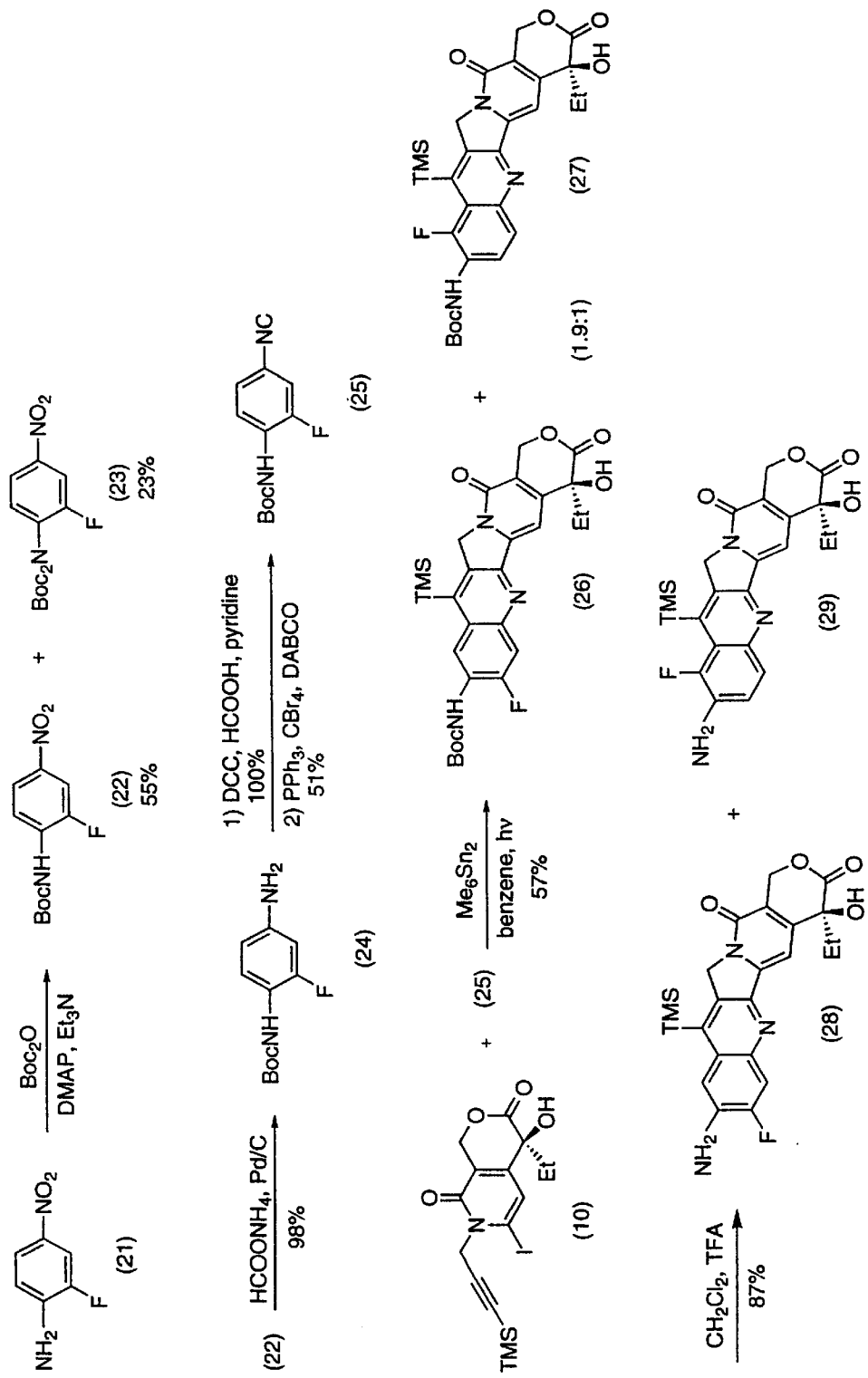
FIG. 5 is an illustration of a synthesis of (20S)-10-amino-11-fluoro-7-trimethylsilylcamptothecin.

Example 10
Preparation of (20S)-11-fluoro-10-amino-7-trimethylsilylcamptothecin (see FIG. 5)

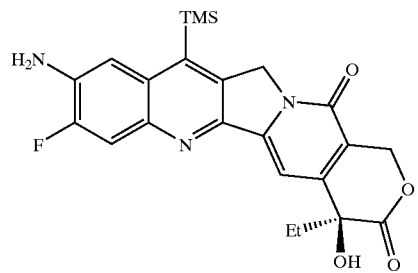

(1) 4-tert-Butyloxycarbonylamino-3-fluoro-1-nitrobenzene (22)

To a solution of 2-fluoro-4-nitroaniline (21) [prepared according to Katritsky, A. R. et al., *J. Org. Chem.*, 51, 5039 (1986)] (2.16 g, 13.9 mmol) in CH₂Cl₂ (25 mL) were successively added di-tert-butyl dicarbonate (3.19 g, 14.6 mmol), triethylamine (2.95 mL, 20.8 mmol) and 4-dimethylaminopyridine (210 mg, 1.67 mmol) and the reaction mixture was stirred 16 h at room temperature. The final solution was diluted with CH₂Cl₂ (75 mL), washed with ice-cooled 5% citric acid (4×50 mL) and dried (Na₂SO₄). After evaporation of the solvent, the residue was subjected to flash-chromatography (Hexanes/AcOEt 9:5) to provide, in order of elution, first 1.95 g (55%) of the mono-protected derivative, 4-tert-butyloxycarbonylamino-3-fluoro-1-nitrobenzene, secondly 1.13 g (23%) of the bis-protected derivative, 4-di-tert-butyloxycarbonylamino-3- fluoro-1-nitrobenzene. The characteristics of the mono-protected derivative are as follows: $^1$H NMR (300 MHz, CDCl$_3$) δ1.52 (s, 9H), 6.99 (br s, 1H), 7.95 (m, 1H), 8.03 (br d, J=9.2 Hz, 1H), 8.34 (br t, J=8.5 Hz, 1H); $^{13}$C NMR (75 MHz, CDCl$_3$) δ28.1, 82.5, 110.9 (d, J$_{CF}$=23 Hz), 118.3, 120.8, 133.5, 141.7, 150.1 (d, J$_{CF}$=243 Hz), 151.4; HRMS (EI) m/z calcd for C$_{11}$H$_{13}$FN$_2$O$_4$ (M$^+$) 256.0859, found 258.0854; LRMS (EI) m/z 256 (M$^+$), 200, 182, 57.

(2) 4-tert-Butyloxycarbonylamino-3-fluoroaniline (24)

Reduction of the nitro group to the amine function was carried out following a classical procedure. See Ram, S. et al., Tetrahedron Lett., 25, 3415 (1984). To a solution of the compound prepared in Example (1) (1.62 g, 6.32 mmol) and ammonium formate (1.70 g, 27 mmol) in anhydrous MeOH (12 mL) was added 10% Pd-C (400 mg) in one portion. After 2 h at room temperature, the final solution was filtered over Celite, concentrated and the residue was directly subjected to flash-chromatography (CHCl$_3$/MeOH 9:1) to provide 1.40 g (98%) of a slightly yellow oil: $^1$H NMR (300 MHz, CD$_3$SOCD$_3$) δ1.40 (s, 9H), 5.22 (s, 2H), 6.25–6.35 (m, 2H), 6.93 (br t, J=8.0 Hz, 1H), 8.29 (br s, 1H); $^{13}$C NMR (75 MHz, CDCl$_3$) δ28.5, 80.4, 102.1 (d, J$_{CF}$=24 Hz), 110.7, 117.2, 122.8, 143.4, 153.1, 154.1 (d, J$_{CF}$= 244 Hz); HRMS (EI) m/z calcd for C$_{11}$H$_{15}$FN$_2$O$_2$ (M$^+$) 226.1118, found 226.1116; LRMS (EI) m/z 226 (M$^+$), 170, 126, 83, 57.

(3) 4-tert-Butyloxycarbonylamino-3-fluorophenyl isonitrile (25)

To a stirred solution of dicyclohexylcarbodiimide (1.51 g, 7.31 mmol) in CH$_2$C$_{12}$ (15 mL) at 0° C. was added formic acid (275 mL, 7.31 mmol) dropwise. After 10 minutes, the resulting mixture was added over a period of 5 minutes to a solution of the compound prepared in Example (2) (1.28 g, 5.66 mmol) in CH$_2$C$_{12}$ (10 mL) and pyridine (0.61 mL, 7.50 mmol) at 0° C. The reaction mixture was then allowed to warm to room temperature and stirred 16 h. After filtration over Celite, the final solution was concentrated and subjected to flash-chromatography (CHCl$_3$/AcOEt 85:15) to give 1.44 g (100%) of 4-tert-butyloxycarbonylamino-3-fluoroformamide, as a white solid. This intermediate (1.38 g, 5.43 mmol) was dissolved in CH$_2$Cl$_2$ (20 mL) and, at 0° C., were successively added tetrabromomethane (1.93 g, 5.80 mmol), triphenylphosphine (1.52 g, 5.80 mmol), and 1.4-diazabicyclo[2.2.2]octane (DABCO, 650 mg, 5.80 mmol). The reaction mixture was allowed to warm to room temperature and stirred 2 h. After evaporation of the solvent, the crude was triturated in ice-cooled Et$_2$O (20 mL) and filtered over Celite. The residue obtained after evaporation of the solvent was purified by flash-chromatography (hexanes/AcOEt 95:5 to 9:1) to provide 660 mg (51%) of a slightly brown solid. $^1$H NMR (300 MHz, CDCl$_3$) δ1.51 (s, 9H), 6.76 (br s, 1H), 7.05–7.20 (m, 2H), 8.17 (br t, J=8.6 Hz, 1H); $^{13}$C NMR (75 MHz, CDCl$_3$) δ28.1, 81.8, 113.3 (d, J$_{CF}$=25 Hz), 119.7, 123.0, 128.6, 150.6 (d, J$_{CF}$=242 Hz), 151.8, 164.2; HRMS (EI) m/z calcd for C$_{12}$H$_{13}$FN$_2$O$_2$ (M$^+$) 236.0961, found 236.0952; LRMS (EI) m/z 236 (M$^+$), 180, 163, 136, 08, 57.

(4) (20S) -10-tert-Butyloxycarbonylamino-11-fluoro-7-trimethylsilyl-camptothecin (26) and (20S)-10-tert-butyloxycarbonylamino-9-fluoro-7-trimethylsilylcamptothecin (27) (mixture respectively 1.9:1)

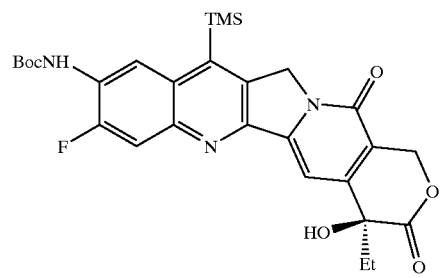

Major

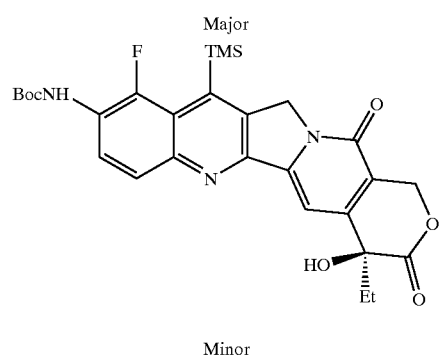

Minor

Following the procedure described in Example 1-(2), the compound prepared in Example 1-(l) (66.8 mg, 0.15 mmol) and the compound described in Example (3) (110 mg, 0.50 mmol) provided, after flash-chromatographies (CHCl$_3$/MeOH 96:4; CHCl$_3$/acetone 10:1), 47.6 mg (57%) of a slighly yellow oil containing the above regioisomers: $^1$H NMR (300 MHz, CDCl$_3$) δ0.54 (d, J=4.9 Hz, 9H$_{minor}$), 0.65 (s, 9H$_{major}$), 0.99 (t, J=7.3 Hz, 3H), 1.86 (m, 2H), 3.93 (br s, 1H), 5.24 (d, J=16.3 Hz, 1H$_{minor}$), 5.25 (br s, 2H$_{major}$), 5.25 (d, J=16.3 Hz, 1H$_{major}$), 5.30 (br s, 2H$_{minor}$), 5.68 (d, J=16.3 Hz, 1H$_{minor}$), 5.69 (d, J=16.3 Hz, 1H$_{major}$), 6–98 (d, J=3.6 Hz, 1H$_{minor}$), 7.02 (d, J=3.6 Hz, 1H$_{major}$), 7.52 (s, 1H$_{minor}$), 7.53 (s, 1H$_{major}$), 7.74 (d, J=12.1 Hz, 1H$_{major}$), 7.92 (br d, J=9.3 Hz, 1H$_{minor}$), 8.60 (br t, J=8.4 Hz, 1H$_{minor}$), 9.08 (d, J=8.7 Hz, 1H$_{major}$); HRMS (EI) m/z calcd for C$_{28}$H$_{32}$FN$_3$O$_6$Si 53.2044, found 553.2022; LRMS (EI) m/z 553 (M$^+$), 493, 479, 53, 435, 424, 409, 394, 380, 353.

(5) (20S)-10-Amino-11-fluoro-7-trimethylsilylcamptothecin (28)

The compound prepared in Example (4) (41.3 mg, 0.0746 mmol) was deprotected following the conditions described in Example 9-(3). After workup, the crude was subjected to a flash-chromatography (CHCl$_3$/acetone/MeOH 70:10:1.5) to provide, in order of elution, first 14.1 mg (42%) of the pure (20S)-10-amino-11-fluoro-7-trimethylsilylcamptothecin, then a 15.2 mg of a c.a. 1:1 mixture of (20S)-10-amino-11-fluoro-7-trimethylsilylcamptothecin and (20S)-10-amino-9-fluoro-7-trimethylsilylcamptothecin. The characteristics of (20S)-10-amino-11-fluoro-7-trimethylsilylcamptothecin are as follows: [α]$^{20}_D$ +20.0 (c 0.2, CHCl$_3$/MeOH 4:1); $^1$H NMR (300 MHz, CDCl$_3$) δ0.59 (s, 9 H), 1.00 (t, J=7.4 Hz, 3H), 1.86 (m, 2H), 3.86 (br s, 1H), 4.31 (br s, 2H), 5.21 (br s, 2H), 5.26 (d, J=16.4 Hz, 1H), 5.69 (d, J=16.4 Hz, 1H), 7.30 (d, J=9.3 Hz, 1H), 7.50 (s, 1H), 7.69 (d, J=11.8 Hz, 1H); $^{13}$C NMR (75 MHz, CDCl$_3$/CD$_3$OD 10:1) δ1.4, 7.7, 31.4, 51.9, 66.1, 72.7, 97.1, 109.4, 113.6 (d, J$_{CF}$=20 Hz), 117.3, 130.8, 134.4, 136.4, 140.2, 142., 146.5, 147.6, 150.6, 153.9, 154.0 (d, J$_{CF}$=251 Hz), 157.6, 173.9; HRMS (EI) m/z calcd for C$_{23}$H$_{24}$FN$_3$O$_4$Si (M$^+$) 453.1520, found 453.1500; LRMS (EI) m/z 453 (M$^+$), 424, 409, 394, 352, 181, 131, 119.

Example 11
Preparation of (20S)-11,12-difluoro-7-trimethylsilylcamptothecin and (20S)-9,10-difluoro-7-trimethylsilylcamptothecin (mixture respectively 3:1)

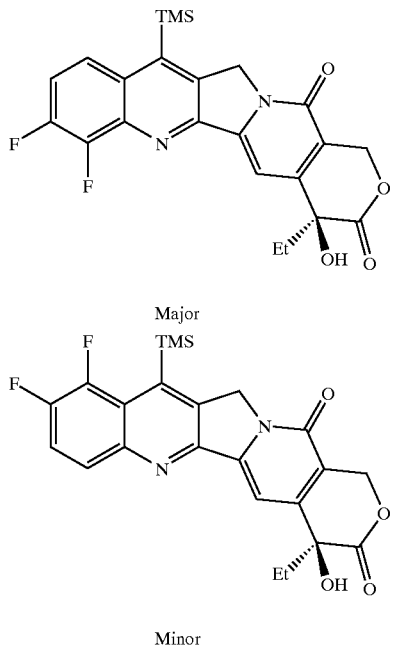

Major

Minor

Following the procedure described in Example 1-(2), the compound prepared in Example 1-(1) (44.5 mg, 0.10 mmol) and 2,3-difluorophenyl isonitrile [prepared in 20% yield following the procedure of Weber, W. P. et al., *Tetrahedron Lett.*, 13, 1637 (1972) with stirring 2 days at room temperature before workup] (42 mg, 0.30 mmol) afforded, after flash-chromatographies (CHCl$_3$/MeOH 95:5; CHCl$_3$/acetone 10:1 to 4:1), 22.6 mg (50%) of a slighly yellow oil containing the above regioisomers: $^1$H NMR (300 MHz, CDCl$_3$) δ0.56 (d, J=4.8 Hz, 1H$_{minor}$), 0.65 (s, 9H$_{major}$), 1.00 (t, J=7.4 Hz, 3H), 1.86 (m, 2H), 3.87 (br s, 1H$_{minor}$), 3.97 (br s, 1H$_{major}$), 5.0–5.47 (m, 3H), 5.68 (d, J=16.5 Hz, 1H), 5.70 (d, J=16.4 Hz, 1H$_{minor}$), 7.31 (m, 1H$_{minor}$), 7.44 (dt, J=9.4, 7.4 Hz, 1H$_{major}$), 7.59 (s, 1H$_{minor}$), 7.60 (5, 1H$_{major}$), 7.68 (m, 1H$_{minor}$), 7.93 (m, 1H$_{major}$); HRMS (EI) m/z calcd for C$_{23}$H$_{22}$F$_2$N$_2$O$_4$Si (M$^+$) 456.1317, found 456.1321; LRMS (EI) m/z 456 (M$^+$), 438, 428, 412, 383, 356, 327.

Example 12
Preparation of 20S-7-triisopropylsilylcamptothecin

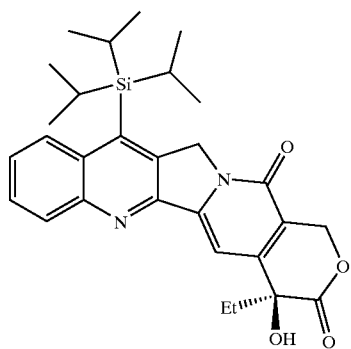

(1) (S)-4-Ethyl-4-hydroxy-6-iodo-3-oxo-7-(triisopropylsilyl-2-propynyl)-1H-pyrano[3,4-c]-8-pyridone Following the procedure outlined in example 1-(1), iodopyridone 2, (200 mg, 0.598 mmol) was combined with triisopropylsilyl-2-propynyl bromide (329 mg, 1.196 mmol). Chromatography (CH$_2$Cl$_2$/AcOEt 9:1) gave 41.1 mg (13%) of a white foam: $^1$H NMR (300 MHz, CDCl$_3$) δ0.91 (t, J=7 Hz, 6H), 0.99 (s, 18H), 1.71 (m, J=7 Hz, 2H), 3.65 (s, 1H), 5.0–5.2 (m, 3H), 5.45 (d, J=16 Hz, 1H), 7.13 (s, 1H); $^{13}$C NMR (75 MHz, CDCl$_3$) δ7.7, 11.2, 18.7, 31.7, 44.6, 66.5, 71.9, 87.7, 100.1, 116.6, 118.2, 148.6, 158.0, 173.4; HRMS (EI) m/z calcd for C$_{22}$H$_{32}$INO$_4$Si (M$^+$) 529.1162, found 529.1145; LRMS (EI) m/z 529 (M$^+$), 486, 442, 82, 59.

(2) (20S)-7-Triisopropylsilylcamptothecin

Following the procedure outlined in example 1-(2), the pyridone described above (41 mg, 0.077 mmol) yielded 23.3 mg (60%) of a light yellow solid: [α]$^{20}_D$ +31.7 (c 0.2, CH$_2$Cl$_2$); IR (CHCl$_3$, cm$^{-1}$) 3026, 3008, 2996, 2962, 2950, 2932, 2892, 2869, 1742, 1658, 1598, 1555, 1466, 1230, 1220, 1158; $^1$H NMR (300 MHz, CDCl$_3$) δ1.02 (t, J=7 Hz, 3H), 1.18 (d, J=7 Hz, 18H), 1.60–2.0 (m, 5H), 2.17 (s, 1H), 5.31 (d, J=16 Hz, 1H), 5.41 (s, 2H), 5.76 (d, J=16, 1H), 7.61 (t, J=7 Hz, 1H), 7.69 (s, 1H), 7.78 (t, J=7 Hz 1H), 8.20 (t, J=7 Hz, 2H); $^{13}$C NMR (125 MHz, CDCl$_3$) 6 7.9, 13.5, 19.2, 31.7, 52.6, 66.5, 72.9, 98.4, 118.6, 127.1, 129.7, 130.2, 130.4, 133.6, 136.3, 145.0, 146.0, 150.3, 150.6, 157.4, 174.1; HRMS (EI) m/z calcd for C$_{29}$H$_{36}$N$_2$O$_4$Si (M$^+$) 504.2444, found 504.2436; LRMS (EI) m/z 504 (M$^+$), 461, 433, 419, 405, 391, 375, 361, 347, 311, 275, 174, 93, 69, 59.

Example 13
Preparation of 20S-7-triisopropylsilylcamptothecin

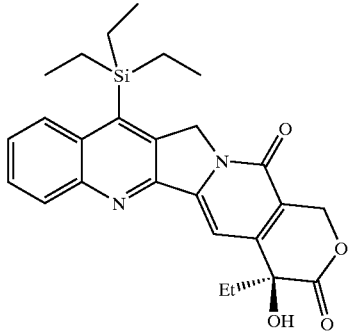

(1) (S)-4-Ethyl-4-hydroxy-6-iodo-3-oxo-7-(triethylsilyl-2-propynyl)-1H-pyrano[3,4-c]-8-pyridone Following the procedure outlined in example 1-(1), iodopyridone 2, (150 mg, 0.450 mmol) was combined with triethylsilyl-2-propynyl bromide (210 mg, 0.90 mmol). Chromatography (CH$_2$Cl$_2$/AcOEt 9:1) gave 97.0 mg (45%) of a white foam: $^1$H NMR (300 MHz, CDCl$_3$) δ0.54 (q, J=8 Hz, 6H), 0.92 (t, J=8 Hz, 12H), 1.74 (m, J=7 Hz, 2H), 3.57 (s, 1H), 4.9–5.1 (m, 3H), 5.46 (d, J=16 Hz, 1H), 7.13 (s, 1H); $^{13}$C NMR (75 MHz, CDCl$_3$) δ4.1, 7.4, 7.6, 31.5, 44.5, 66.3, 71.8, 88.7, 99.2, 100.0, 116.5, 118.1, 148.5, 158.0, 173.2; HRMS (EI) m/z calcd for C$_{19}$H$_{26}$INO$_4$Si (M$^+$) 487.0676, found 487.0688; LRMS (EI) m/z 487 (M$^+$), 458, 430, 420, 402, 360, 332, 153, 141, 125, 96, 83, 68, 57.

(2) (20S)-7-Triethylsilylcamptothecin

Following the procedure outlined in example 1-(2), the pyridone described above (48.7 mg, 0.1 mmol) yielded 29.8 mg (65%) of a light yellow solid: $[\alpha]^{20}_D$ +35.9 (c 0.2, $CH_2Cl_2$); IR ($CHCl_3$, $cm^{-1}$) 3015, 3002, 2960, 2935, 1741, 1658, 1599, 1219, 1199, 1158; $^1H$ NMR (300 MHz, $CDCl_3$) δ0.80–1.00 (m, 12H), 1.0–1.18 (m, 6H), 1.70–1.90 (m, 2H), 5.22–5.27 (m, 3H), 5.69 (d, J=16 Hz, 1H), 7.58 (t, J 7 Hz, 1H), 7.63 (s, 1H), 7.72 (t, J=7 Hz 1H), 8.18 (m, 2H); $^{13}C$ NMR (125 MHz, $CDCl_3$) δ5.0, 7.6, 7.9, 31.7, 52.1, 66.5, 72.9, 97.7, 118.3, 127.4, 127.9, 129.7, 131.2, 132.6, 136.1, 142.6, 146.6, 147.9, 150.2, 150.9, 157.6, 174.1; HRMS (EI) m/z calcd for $C_{26}H_{30}N_2O_4Si$ (M⁺) 462.1975, found 462.1982; LRMS (EI) m/z 462 (M⁺), 433, 418, 405, 389, 361, 256, 220, 205, 189, 178, 149, 137, 123, 109, 95, 81, 69, 57.

Example 14
Preparation of (20S)-7-(dimethyl-(1'S,2'S,5'S) 7,7 dimethylnorpinylsilyl)camptothecin

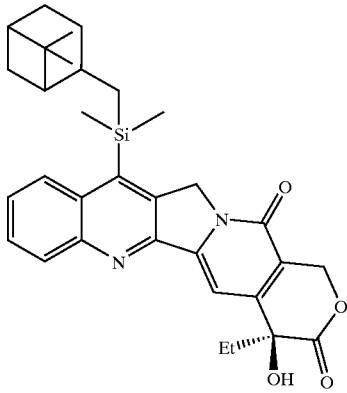

(1) (S)-4-Ethyl-4-hydroxy-6-iodo-3-oxo-7-(dimethyl-(1S, 2S, 5S) 7,7 dimethylnorpinylsilyl-2-propynyl)-1H-pyrano[3,4-c]-8-pyridone Following the procedure outlined in example 1-(1), iodopyridone 2 (150 mg, 0.450 mmol) was combined with dimethyl-(1S, 2S, 5S)7,7 dimethylnorpinylsilyl-2-propynyl bromide (281 mg, 0.90 mmol). Chromatography ($CH_2Cl_2$/AcOEt 9:1) gave 100.8 mg (39%) of a white foam: $^1H$ NMR (300 MHz, $CDCl_3$) δ0.10 (d, J=2 Hz, 6H), 0.48–0.70 (m, 2H), 0.72 (s, 3H), 0.93 (t, J=7 Hz, 3H), 1.10 (s, 3H), 1.15–1.40 (m, 3H), 1.60–1.85 (m, 6H), 1.88–2.00 (m, 1H), 2.05–2.20 (m, 1H), 3.58 (s, 1H), 4.95 (m, 3H), 5.46 (d, J=16 Hz, 1H), 7.13 (s, 1H); $^{13}C$ NMR (75 MHz, $CDCl_3$) δ0.78, 7.8, 20.2, 23.1, 24.0, 24.8, 25.3, 27.0, 31.3,. 31.7, 39.7, 40.7, 44.7, 49.1, 66.5, 71.9, 91.0, 98.5, 100.3, 116.6, 118.3, 148.7, 158.0, 173.4.

(2) (20S)-7-(dimethyl-1'S,2'S,5'S) 7,7 dimethylnorpinylsilyl)camptothecin

Following the procedure outlined in example 1-(2), the pyridone described above (57.0 mg, 0.1 mmol) yielded 29.4 mg (54%) of a light yellow solid: $[\alpha]^{20}$ +29.2 (c 0.2, $CH_2Cl_2$); IR ($CHCl_3$, $cm^{-1}$) 3020, 3000, 2980, 2972, 2939, 2914, 2824, 2867, 1741, 1658, 1599, 1556, 1264, 1231, 1201, 1157, 843; $^1H$ NMR (300 MHz, $CDCl_3$) δ0.50–0.70 (m, 8H), 0.90–1.10 (m, 9H), 1.10–1.35 (m, 4H), 1.40–1.60 (m, 3H), 1.72 (m, 1H), 1.80–1.95 (m, 2H), 2.05–2.11 (m, 2H), 5.25 (d, J=16 Hz 1H), 5.27 (s, 2H), 5.69 (d, J=16 Hz, 1H), 7.58 (t, J=8 Hz, 1H), 7.62 (s, 1H), 7.72 (t, J=8 Hz, 1H), 8.10–8.2 (m, 2H); $^{13}C$ NMR (125 MHz, $CDCl_3$) δ1.4, 7.9, 19.9, 23.0, 24.6, 25.3, 26.8, 31.6, 31.7, 39.6, 40.5, 49.3, 52.0, 66.5, 72.9, 97.7, 118.3, 127.3, 128.3, 129.7, 131.2, 132.1, 134.6, 144.6, 146.6, 148.0, 150.2, 150.9, 157.6, 174.0; HRMS (EI) m/z calcd for $C_{32}H_{38}N_2O_4Si$ (M⁺) 542.2601, found 542.2588; LRMS (EI) m/z 542 (M⁺), 498, 487, 460, 443, 431, 406, 387, 377, 362, 333, 318, 304, 289, 275, 219, 178, 166, 141, 115, 95, 67.

Example 15
(20S)-7-(3-cyanopropyldimethylsilyl)camptothecin

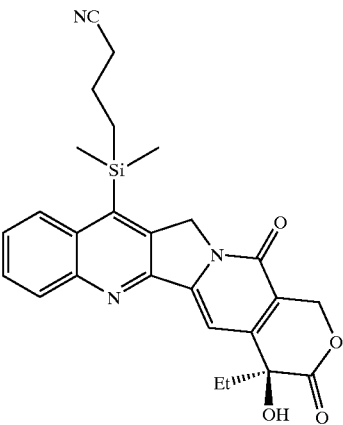

(1) (S)-4-Ethyl-4-hydroxy-6-iodo-3-oxo-7-(3-cyanopropyldimethylsilyl-2-propynyl)-1H-pyrano[3,4-c]-8-pyridone Following the procedure cited by Rico and co-workers (J. Org. Chem. 1994, 59, 415), iodopyridone 2, (150 mg, 0.450 mmol) was combined with 3-cyanopropyldimethylsilyl-2-propynyl bromide (165 mg, 0.678 mmol), $K_2CO_3$ (124 mg, 0.90 mmol), $Bu_4N^+Br^-$ (14.5 mg, 0.045 mmol), $H_2O$ (0.02 mL) and toluene (3.6 mL). This mixture was refluxed for 1 h. After filtration and chromatography ($CH_2Cl_2$/AcOEt 9:1) 34.0 mg (15%) of a white oil was obtained: $^1H$ NMR (300 MHz, $CDCl_3$) δ0.17 (s, 6H), 0.70–0.80 (m, 2H), 0.98 (t, J=7 Hz, 3H), 1.70–1.90 (m, 4H), 2.39 (t, J=7, 2H), 3.66 (s, 1H), 4.9–5.22 (m, 3H), 5.51 (d, J=16 Hz, 1H), 7.19 (s, 1H); $^{13}C$ NMR (125 MHz, $CDCl_3$) δ–2.1, 7.8, 15.4, 20.5, 20.6, 31.6, 44.6, 66.4, 71.9, 89.1, 99.6, 100.0, 116.7, 118.3, 119.7, 148.8, 158.0, 173.3; HRMS (EI) m/z calcd for $C_{19}H_{23}IN_2O_4Si$ (M⁺) 498.0472, found 498.0480; LRMS (EI) m/z 498 (M⁺), 483, 470, 445, 430, 416, 402, 392, 371, 348, 335, 306, 290, 266, 223, 202, 185, 163, 136, 126, 109, 98, 81, 69, 57.

(2) (20S)-7-(3-cyanopropyldimethylsilyl)camptothecin

Following the procedure outlined in example 1-(2), the pyridone described above (25.0 mg, 0.05 mmol) yielded 9.8 mg (41%) of a light yellow solid: $[\alpha]^{20}_D$ +34.3 (c 0.2, $CH_2Cl_2$); IR ($CHCl_3$, $cm^{-1}$) 3025, 3016, 1741, 1659, 1600, 1264, 1222; $^1H$ NMR (300 MHz, $CDCl_3$) δ0.71 (s, 6H), 1.05 (t, J=7 Hz,3H), 1.26 (m, 2H),1.66 (m, 2H), 1.90 (m, 2H), 2.35 (t, J=7 Hz, 2H), 3.76 (s, 1H), 5.31 (d, J=16 Hz, 1H), 5.31 (s, 2H), 5.75 (d, J=16 Hz, 1H), 7.67 (m, 2H), 7.82 (t, J=8 Hz, 1H), 8.17 (d, J=8 Hz 1H), 8.24 (d, J=8 Hz, 1H); $^{13}C$ NMR (125 MHz, $CDCl_3$) δ0.2, 7.9, 16.8, 20.7, 20.73, 31.7, 50.9, 66.5, 72.8, 97.9, 118.5, 119.2, 127.7, 127.8, 130.0, 131.4, 131.9, 135.2, 141.9, 146.3, 148.1, 150.3, 151.1, 157.5, 174.0; HRMS (EI) m/z calcd for $C_{26}H_{27}N_3O_4Si$ (M⁺) 473.1771, found 473.1755; LRMS (EI) m/z 473 (M⁺), 444, 429, 414, 400, 389, 373 362, 344, 331, 303, 289, 2.75, 245, 219, 166, 152, 130, 98, 71.

Example 16

Preparation of (20S)-7-(3-halopropyldimethylsilyl)camptothecin

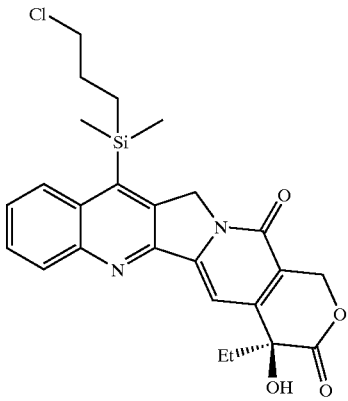

(1) (S)-4-Ethyl-4-hydroxy-6-iodo(and 6-bromo)-3-oxo-7-(3-chloropropyldimethylsilyl-2-propynyl)-1H-pyrano[3,4-c]-8-pyridone

Following the procedure outlined in example 1-(1), [iodopyridone 2 (150 mg, 0.450 mmol) was combined with 3-chloropropyldimethylsilyl-2-propynyl bromide (228 mg, 0.90 mmol). Chromatography (CH$_2$Cl$_2$/AcOEt 9:1) gave 75.4 mg (33%) of a clear oil. Analysis of the NMR showed the presence of the alkyl bromide in addition to the desired chloro derivative in a 1.6:1 ratio in favor of the former.: $^1$H NMR (300 MHz, CDCl$_3$) δ0.09 (s, 6H), 0.60–0.70 (m, 2H), 0.85–0.89 (t, J=7 Hz, 3H), 1.60–1.95 (m, 4H), 3.33 (t, J=7 Hz, 2H, assigned to iodo), 3.44 (t, J=7 Hz, 2H, assigned to bromo), 3.75 (s, 1H), 4.91–5.18 (m, 3H), 5.42 (d, J=16 Hz, 1H), 7.12 (s, 1H).

(2) (20S)-7-(3-halopropyldimethylsilyl)camptothecin

Following the procedure outlined in example 1-(2), the pyridone described above (51 mg, 0.1 mmol) yielded 23 mg (49%) of a light yellow solid. Analysis of the spectral data identified this solid as a 3 component mixture corresponding to the chloro, bromo and the iodo derivatives in a 1.6:1:1.3 ratio: [α]$^{20}_D$ +30.8 (c 0.2, CH$_2$Cl$_2$); IR (CHCl$_3$, cm$^{-1}$) 3029, 3012, 2980, 2963, 2933, 1742, 1658, 1600, 1556, 1258, 1233, 1218, 1200, 1158, 1045, 843, 822, 794; $^1$H NMR (300 MHz, CDCl$_3$) δ0.69 (s, 6H), 1.04 (t, J=7 Hz, 3H), 1.18–1.30 (m, 2H), 1.60–2.0 (m, 4H), 3.15 (t, J=7 Hz, 2H, assigned to iodo), 3.36 (t, J=7 Hz, 2H, assigned to bromo), 3.48 (t, J=7 Hz, 2H, assigned to chloro), 3.88 (s, 1H), 5.30 (d, J=16 Hz, 1H), 5.31 (s, 2H);, 5.74 (d, J=16 Hz, 1H), 7.62–7.66 (m, 2H), 7.87 (t, J=8 Hz, 1H), 8.18 (d, J=8 Hz, 1H), 8.22 (d, J=8 Hz, 1H); $^{13}$C NMR (125 MHz, CDCl$_3$) δ0.2, 7.9, 14.7, 27.5, 31.7, 47.4, 51.9, 66.4, 72.8, 98.2, 118.6, 127.7, 127.9, 130.0, 131.0, 132.0, 135.2, 146.1, 147.6, 150.2, 157.5, 174.0; HRMS (EI) m/z calcd for C$_{25}$H$_{27}$ClN$_2$O$_4$Si (M$^+$) 482.1429, found 482.1413; LRMS (EI) m/z 482 (M$^+$), 453, 438, 361, 305, 275.

Example 17

Preparation of (20S)10-acetoxy-7-tert-butyldimethylsilylcamptothecin

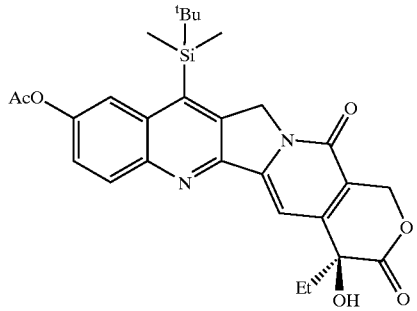

Following the procedure outlined in example 1-(2), the pyridone described above (34.5 mg, 0.071 mmol) and p-acetoxyisonitrile yielded 21.3 mg (58%) of a light yellow solid: [α]$^{20}_D$ +36.2 (c 0.2, CH$_2$Cl$_2$); IR (CHCl$_3$, cm$^{-1}$) 3029, 3000, 2958, 2931, 2902, 2885, 2859, 1742, 1659, 1600, 1557, 1504, 1464, 1371, 1256, 1232, 1195, 1166, 1045; $^1$H NMR (300 MHz, CDCl$_3$) δ0.69 (s, 6H), 0.90 (s, 9H), 1.04 (t, J=7 Hz, 3H), 1.80–2.00 (m, J=7 Hz, 2H), 2.40 (s, 3H), 3.81 (s, 1H), 5.30 (d, J=16 Hz 1H), 5.31. (s, 2H), 5.75 (d, J=16 Hz, 1H), 7.53 (dd, J$_1$=9 Hz, J$_2$=2 Hz, 1H), 7.65 (s, 1H), 8.08 (d, J=2 Hz, 1H), 8.21 (d, J=9 Hz, 1H); $^{13}$C NMR (125 MHz, CDCl$_3$) δ0.6, 7.9, 19.3, 21.5, 27.2, 31.7, 52.5, 66.5, 72.9, 97.7, 118.4, 120.4, 124.8, 132.1, 133.2, 136.7, 142.8, 146.2, 146.4, 149.0, 150.2, 150.8, 157.5, 169.1, 174.1; LRMS (EI) m/z 520 (M$^+$), 478, 463, 421, 377, 347, 320, 291, 57.

Example 18

(2) (20S)10-Acetoxy-7-tert-butyldimethylsilylcamptothecin

Following the procedure outlined in example 2-(2), the pyridone described above (34.5 mg, 0.071 mmol) yielded, using the same chromatographic conditions, 21.3 mg (58%) of a light yellow solid: [α]$^{20}_D$ +36.2 (c 0.2, CH$_2$Cl$_2$); IR (CHCl$_3$, cm$^{-1}$) 3029, 3000, 2958, 2931, 2902, 2885, 2859, 1742, 1659, 1600, 1557, 1504, 1464, 1371, 1256, 1232, 1195, 1166, 1045; $^1$H NMR (300 MHz, CDCl$_3$) δ0.69 (s, 6H), 0.90 (s, 9H), 1.04 (t, J=7 Hz, 3H), 1.80–2.00 (m, J=7 Hz, 2H), 2.40 (s, 3H), 3.81 (s, 1H), 5.30 (d, J=16 Hz, 1H), 5.31.(s, 2H), 5.75 (d, J=16 Hz, 1H), 7.53 (dd, J$_1$=9 Hz, J$_2$=2 Hz, 1H), 7.65 (s, 1H), 8.08 (d, J=2 Hz, 1H), 8.21 (d, J=9 Hz, 1H); $^{13}$C NMR (125 MHz, CDCl$_3$) δ0.6, 7.9, 19.3, 21.5, 27.2, 31.7, 52.5, 66.5, 72.9, 97.7, 118.4, 120.4, 124.8, 132.1, 133.2, 136.7, 142.8, 146.2, 146.4, 149.0, 150.2, 150.8, 157.5, 169.1, 174.1; HRMS (EI) m/z calcd for C$_{28}$H$_{32}$N$_2$O$_6$Si (M$^+$) 520.2030, found 520.2014 LRMS (EI) m/z 520 (M$^+$), 478, 463, 421, 377, 347, 320, 291, 57.

Example 19

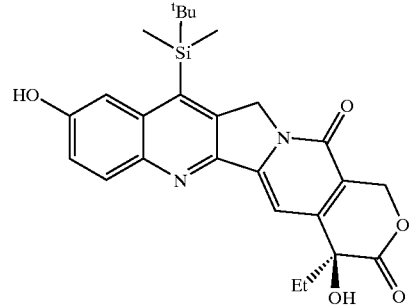

(20S)10-Hydroxy-7-tert-butyldimethylsilylcamptothecin

Following the procedure outlined in example 5, (13.4 mg, 0.026 mmol) of the compound described in example 18 was converted to the hydroxy derivative. Purification (2:1 CH$_2$Cl$_2$:Acetone) on a preparative TLC plate gave 10.6 mg (85%) of a yellow solid: [α]$^{20}_D$ +17.4 (c 0.2, 3:1 CH$_2$Cl$_2$/MeOH); $^1$H NMR (300 MHz, 3:1 CDCl$_3$/CD$_3$OD) δ0.66 (s, 6H), 0.88–1.05 (m, 12H), 1.80–2.00 (m, 2H), 5.25–5.30 (m, 3H), 5.70 (d, J=16 Hz, 1H), 7.37 (dd, J$_1$=9 Hz, J$_2$=2 Hz, 1H), 7.54 (d, J=2 Hz, 1H), 7.60 (s, 1H), 8.05 (d, J=9 Hz, 1H); $^{13}$C NMR (125 MHz, (3:1) CDCl$_3$:CD$_3$OD) δ8.1, 20.6, 27.6, 30.4, 31.9, 53.6, 66.5, 73.9, 98.6, 112.1, 118.8, 123.3, 132.1, 135.6, 137.4, 141.6, 143.8, 147.3, 148.4, 152.6, 157.5, 158.7, 174.7; HRMS (EI) m/z calcd for C$_{26}$H$_{30}$N$_2$O$_5$Si (M$^+$) 478.1924, found 478.1947 LRMS (EI) m/z 478 (M$^+$), 434, 421, 377, 304, 284, 227, 178, 149, 137, 109, 97, 83, 69, 57.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A compound having the structure:

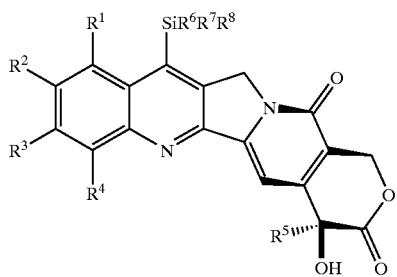

wherein R$^1$ is hydrogen, an alkyl group, an alkenyl group, an alkynyl group, an alkoxyl group, an aryloxy group, a carbamoyloxy group, a halogen, a hydroxyl group, a nitro group, a cyano group, an azido group, a formyl group, a hydrazino group, —C(O)R$^f$, wherein R$^f$ is an alkyl group, a haloalkyl group, an alkoxyl group, an amino group or a hydroxyl group, an amino group, —SR$^c$, wherein R$^c$ is hydrogen, —C(O)R$^f$, an alkyl group, or an aryl group, —OC(O)R$^d$ or —OC(O)OR$^d$, wherein R$^d$ is an alkyl group;

wherein R$^2$ is an alkenyl group, an alkynyl group, an alkoxyl group, an aryloxy group, a carbamoyloxy group, a halogen, a nitro group, a cyano group, an azido group, a formyl group, a hydrazino group, —C(O)R$^f$, wherein R$^f$ is an alkyl group, a haloalkyl group, an alkoxyl group, an amino group or a hydroxyl group, an amino group, —SR$^c$, wherein R$^c$ is hydrogen, —C(O)R$^f$, an alkyl group, or an aryl group, —OC(O)R$^d$ or —OC(O)OR$^d$, wherein R$^d$ is an alkyl group; or R$^1$ and R$^2$ together form a group of the formula —O(CH$_2$)$_n$O— wherein n represents the integer 1 or 2;

R$^3$ is H, F, a halogen atom, a nitro group, an amino group, a hydroxyl group, or a cyano group; or R$^2$ and R$^3$ together form a group of the formula —O(CH$_2$)$_n$O— wherein n represents the integer 1 or 2;

R$^4$ is H, F, a C$_{1-3}$ alkyl group, a C$_{2-3}$ alkenyl group, a C$_{2-3}$ alkynyl group, or a C$_{1-3}$ alkoxyl group;

R$^5$ is a C$_{1-10}$ alkyl group, or a propargyl group; and

R$^6$, R$^7$ and R$^8$ are independently a C$_{1-10}$ alkyl group, a C$_{2-10}$ alkenyl group, a C$_{2-10}$ alkynyl group, an aryl group or a —(CH$_2$)$_N$R$^9$ group, wherein N is an integer within the range of 1 through 10 and R$^9$ is a hydroxyl group, alkoxy group, an amino group, an alkylamino group, a dialkylamino group, a halogen atom, a cyano group or a nitro group;

and pharmaceutically acceptable salts thereof.

2. A compound having the structure:

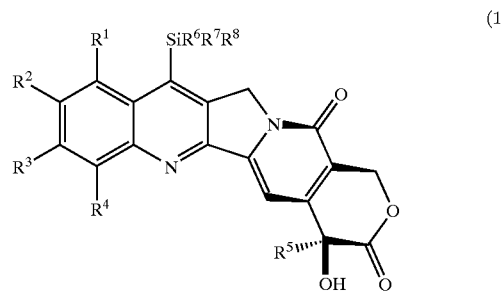

wherein R$^1$ is an alkenyl group, an alkynyl group, an alkoxyl group, an aryloxy group, a carbamoyloxy group, a halogen, a hydroxyl group, a nitro group, a cyano group, an azido group, a formyl group, a hydrazino group, —C(O)R$^f$, wherein R$^f$ is an alkyl group, a haloalkyl group, an alkoxyl group, an amino group or a hydroxyl group, an amino group, —SR$^c$, wherein R$^c$ is hydrogen, —C(O)R$^f$, an alkyl group, or an aryl group, —OC(O)R$^d$ or —OC(O)OR$^d$, wherein R$^d$ is an alkyl group;

wherein R$^2$ is hydrogen, an alkyl group, an alkenyl group, an alkynyl group, an alkoxyl group, an aryloxy group, a carbamoyloxy group, a halogen, a hydroxyl group, a nitro group, a cyano group, an azido group, a formyl group, a hydrazino group, —C(O)R$^f$, wherein R$^f$ is an alkyl group, a haloalkyl group, an alkoxyl group, an amino group or a hydroxyl group, an amino group, —SR$^c$, wherein R$^c$ is hydrogen, —C(O)R$^f$, an alkyl group, or an aryl group, —OC(O)R$^d$ or —OC(O)OR$^d$, wherein R$^d$ is an alkyl group; or R$^1$ and R$^2$ together form a group of the formula —O(CH$_2$)$_n$O— wherein n represents the integer 1 or 2;

R$^3$ is H, F, a halogen atom, a nitro group, an amino group, a hydroxyl group, or a cyano group; or R$^2$ and R$^3$ together form a group of the formula —O(CH$_2$)$_n$O— wherein n represents the integer 1 or 2;

R$^4$ is H, F, a C$_{1-3}$ alkyl group, a C$_{2-3}$ alkenyl group, a C$_{2-3}$ alkynyl group, or a C$_{1-3}$ alkoxyl group;

R$^5$ is a C$_{1-10}$ alkyl group, or a propargyl group; and

R$^6$, R$^7$ and R$^8$ are independently a C$_{1-10}$ alkyl group, a C$_{2-10}$ alkenyl group, a C$_{2-10}$ alkynyl group, an aryl group or a —(CH$_2$)$_N$R$^9$ group, wherein N is an integer within the range of 1 through 10 and R$^9$ is a hydroxyl group, alkoxy group, an amino group, an alkylamino group, a dialkylamino group, a halogen atom, a cyano group or a nitro group;

and pharmaceutically acceptable salts thereof.

3. A compound having the structure:

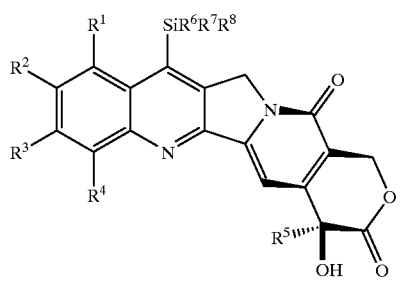

(1)

wherein $R^1$ is hydrogen, an alkyl group, an alkenyl group, an alkynyl group, an alkoxyl group, an aryloxy group, a carbamoyloxy group, a halogen, a hydroxyl group, a nitro group, a cyano group, an azido group, a formyl group, a hydrazino group, —C(O)$R^f$, wherein $R^f$ is an alkyl group, a haloalkyl group, an alkoxyl group, an amino group or a hydroxyl group, an amino group, —$SR^c$, wherein $R^c$ is hydrogen, —C(O)$R^f$, an alkyl group, or an aryl group, —OC(O)$R^d$ or —OC(O)O$R^d$, wherein $R^d$ is an alkyl group;

wherein $R^2$ is hydrogen, an alkyl group, an alkenyl group, an alkynyl group, an alkoxyl group, an aryloxy group, a carbamoyloxy group, a halogen, a hydroxyl group, a nitro group, a cyano group, an azido group, a formyl group, a hydrazino group, —C(O)$R^f$, wherein $R^f$ is an alkyl group, a haloalkyl group, an alkoxyl group, an amino group or a hydroxyl group, an amino group, —$SR^c$, wherein $R^c$ is hydrogen, —C(O)$R^f$, an alkyl group, or an aryl group, —OC(O)$R^d$ or —OC(O)O$R^d$, wherein $R^d$ is an alkyl group; or $R^1$ and $R^2$ together form a group of the formula —O(CH$_2$)$_n$O— wherein n represents the integer 1 or 2;

$R^3$ is a halogen atom, a nitro group, an amino group, a hydroxyl group, or a cyano group; or $R^2$ and $R^3$ together form a group of the formula —O(CH$_2$)$_n$O— wherein n represents the integer 1 or 2;

$R^4$ is H, F, a $C_{1-3}$ alkyl group, a $C_{2-3}$ alkenyl group, a $C_{2-3}$ alkynyl group, or a $C_{1-3}$ alkoxyl group;

$R^5$ is a $C_{1-10}$ alkyl group, or a propargyl group; and $R^6$, $R^7$ and $R^8$ are independently a $C_{1-10}$ alkyl group, a $C_{2-10}$ alkenyl group, a $C_{2-10}$ alkynyl group, an aryl group or a —(CH$_2$)$_N$$R^9$ group, wherein N is an integer within the range of 1 through 10 and $R^9$ is a hydroxyl group, alkoxy group, an amino group, an alkylamino group, a dialkylamino group, a halogen atom, a cyano group or a nitro group;

and pharmaceutically acceptable salts thereof.

4. A compound having the structure:

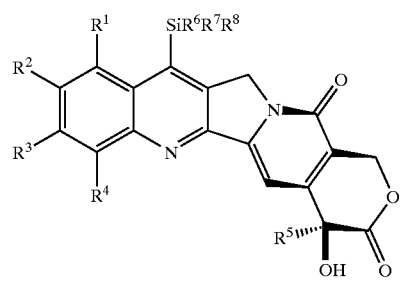

(1)

wherein $R^1$ is hydrogen, an alkyl group, an alkenyl group, an alkynyl group, an alkoxyl group, an aryloxy group, a carbamoyloxy group, a halogen, a hydroxyl group, a nitro group, a cyano group, an azido group, a formyl group, a hydrazino group, —C(O)$R^f$, wherein $R^f$ is an alkyl group, a haloalkyl group, an alkoxyl group, an amino group or a hydroxyl group, an amino group, —$SR^c$, wherein $R^c$ is hydrogen, —C(O)$R^f$, an alkyl group, or an aryl group, —OC(O)$R^d$ or —OC(O)O$R^d$, wherein $R^d$ is an alkyl group;

wherein $R^2$ is hydrogen, an alkyl group, an alkenyl group, an alkynyl group, an alkoxyl group, an aryloxy group, a carbamoyloxy group, a halogen, a hydroxyl group, a nitro group, a cyano group, an azido group, a formyl group, a hydrazino group, —C(O)$R^f$, wherein $R^f$ is an alkyl group, a haloalkyl group, an alkoxyl group, an amino group or a hydroxyl group, an amino group, —$SR^c$, wherein $R^c$ is hydrogen, —C(O)$R^f$, an alkyl group, or an aryl group, —OC(O)$R^d$ or —OC(O)O$R^d$, wherein $R^d$ is an alkyl group; or $R^1$ and $R^2$ together form a group of the formula —O(CH$_2$)$_n$O— wherein n represents the integer 1 or 2;

$R^3$ is H, F, a halogen atom, a nitro group, an amino group, a hydroxyl group, or a cyano group; or $R^2$ and $R^3$ together form a group of the formula —O(CH$_2$)$_n$O— wherein n represents the integer 1 or 2;

$R^4$ is F, a $C_{2-3}$ alkenyl group, a $C_{2-3}$ alkynyl group, or a $C_{1-3}$ alkoxyl group;

$R^5$ is a $C_{1-10}$ alkyl group, or a propargyl group; and $R^6$, $R^7$ and $R^8$ are independently a $C_{1-10}$ alkyl group, a $C_{2-10}$ alkenyl group, a $C_{2-10}$ alkynyl group, an aryl group or a —(CH$_2$)$_N$$R^9$ group, wherein N is an integer within the range of 1 through 10 and $R^9$ is a hydroxyl group, alkoxy group, an amino group, an alkylamino group, a dialkylamino group, a halogen atom, a cyano group or a nitro group;

and pharmaceutically acceptable salts thereof.

5. The compound of claim 1 wherein at least one of $R^1$ and $R^2$ is independently an amino group.

6. The compound of claim 2 wherein at least one of $R^1$ and $R^2$ is independently an amino group.

7. The compound of claim 3 wherein at least one of $R^1$ and $R^2$ is independently an amino group.

8. The compound of claim 4 wherein at least one of $R^1$ and $R^2$ is independently an amino group.

* * * * *